(12) United States Patent
Michelotti et al.

(10) Patent No.: US 7,612,200 B2
(45) Date of Patent: Nov. 3, 2009

(54) INHIBITORS OF PROTEIN KINASES

(75) Inventors: Enrique Luis Michelotti, Fort Washington, PA (US); William R. Moore, Jr., Devon, PA (US); Eric Bruce Springman, East Norriton, PA (US)

(73) Assignee: Locus Pharmaceuticals, Inc., Blue Bell, PA (US)

( * ) Notice: Subject to any disclaimer, the term of this patent is extended or adjusted under 35 U.S.C. 154(b) by 408 days.

(21) Appl. No.: 11/295,433

(22) Filed: Dec. 7, 2005

(65) Prior Publication Data

US 2009/0192307 A1 Jul. 30, 2009

Related U.S. Application Data

(60) Provisional application No. 60/633,726, filed on Dec. 7, 2004.

(51) Int. Cl.
C07D 285/36 (2006.01)
(52) U.S. Cl. .............. 540/545; 540/575; 544/360; 544/60
(58) Field of Classification Search ............... 540/545
See application file for complete search history.

(56) References Cited

U.S. PATENT DOCUMENTS

| | | | |
|---|---|---|---|
| 5,569,654 A | 10/1996 | Armour et al. |
| 5,599,930 A | 2/1997 | Romero et al. |
| 5,696,110 A | 12/1997 | Bourrain et al. |
| 5,763,437 A | 6/1998 | Sato et al. |
| 5,942,387 A | 8/1999 | Hollinshead |
| 6,080,763 A | 6/2000 | Regan et al. |
| 6,187,799 B1 | 2/2001 | Wood et al. |
| 6,228,881 B1 | 5/2001 | Regan et al. |
| 6,242,453 B1 | 6/2001 | Cirillo et al. |
| 6,297,381 B1 | 10/2001 | Cirillo et al. |
| 6,329,415 B1 | 12/2001 | Cirillo et al. |
| 6,333,325 B1 | 12/2001 | Cirillo et al. |
| 6,358,945 B1 | 3/2002 | Breitfelder et al. |
| 6,372,773 B1 | 4/2002 | Regan |
| 6,492,393 B1 | 12/2002 | Breitfelder et al. |
| 6,506,747 B1 | 1/2003 | Betageri et al. |
| 6,506,748 B2 | 1/2003 | Hickey et al. |
| 6,525,046 B1 | 2/2003 | Cirillo et al. |
| 6,627,629 B2 | 9/2003 | Ko et al. |
| 6,656,933 B2 | 12/2003 | Hickey |
| 2003/0069284 A1 | 4/2003 | Keegan et al. |
| 2003/0212070 A1 | 11/2003 | Schwink et al. |
| 2003/0225053 A1 | 12/2003 | Gao et al. |
| 2004/0122235 A1 | 6/2004 | Polisetti et al. |
| 2004/0259912 A1 | 12/2004 | Matsumoto et al. |
| 2005/0239841 A1 | 10/2005 | Browning et al. |
| 2006/0009453 A1 | 1/2006 | Geuns-Meyer et al. |
| 2006/0014761 A1 | 1/2006 | Morgan et al. |
| 2006/0069102 A1 | 3/2006 | Leban et al. |
| 2006/0167247 A1 | 7/2006 | Michelotti et al. |

FOREIGN PATENT DOCUMENTS

| | | |
|---|---|---|
| WO | WO 98/52558 A1 | 11/1998 |
| WO | WO 98/52559 A1 | 11/1998 |
| WO | WO 99/32111 * | 1/1999 |
| WO | WO 99/32110 A1 | 7/1999 |
| WO | WO 99/32111 A1 | 7/1999 |
| WO | WO 99/32463 A1 | 7/1999 |
| WO | WO 00/41698 A1 | 7/2000 |
| WO | WO 00/43384 A1 | 7/2000 |
| WO | WO 00/55139 A3 | 9/2000 |
| WO | WO 00/55152 A1 | 9/2000 |
| WO | WO 01/36403 A1 | 5/2001 |
| WO | WO 02/083628 A1 | 10/2002 |
| WO | WO 02/083642 A1 | 10/2002 |
| WO | WO 02/085859 A1 | 10/2002 |
| WO | WO 02/092576 A1 | 11/2002 |
| WO | WO 02/096876 A1 | 12/2002 |
| WO | WO 02/098869 A2 | 12/2002 |

(Continued)

OTHER PUBLICATIONS

Attanasi, O.A., et al., "Conjugated Azoalkenes. Part 12. Synthesis of New 1-Amino-3-cyanopyrrole, 1,2-Diaminopyrrole and Pyrrolo[2,3-b]pyrrole Derivatives by Reaction of Some Conjugated Azoalkenes with Activated Nitriles," *J. Chem. Soc. Perkin Trans.* 1:1009-1014, Journal of the Chemical Society (1992).

Burak, K., and Machon, Z., "Synthesis of isothiazole derivatives with potential biological activity," *Pharmazie* 47:492-495, Govi-Verlag, Pharmazeutischer Verlag GmbH (1992).

(Continued)

*Primary Examiner*—James O Wilson
*Assistant Examiner*—Brian McDowell
(74) *Attorney, Agent, or Firm*—Pepper Hamilton LLP

(57) ABSTRACT

The present invention is directed to a compound having the formula

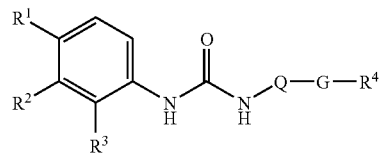

wherein $R^1$, $R^2$, $R^3$, $R^4$, G, and Q are defined herein. The compounds of the present invention are useful as inhibitors of protein kinases. The present invention is also directed to compositions comprising a compound according to the above formula. The present invention is also directed to compounds that stabilize the open conformation of a protein kinase, a crystallized protein kinase in the open conformation, and uses thereof. The compounds and compositions described herein are useful for treating and preventing an inflammatory condition or disease.

1 Claim, No Drawings

FOREIGN PATENT DOCUMENTS

| | | |
|---|---|---|
| WO | WO 03/005999 A2 | 1/2003 |
| WO | WO 03/049742 A1 | 6/2003 |
| WO | WO 03/068229 A1 | 8/2003 |
| WO | WO 03/068746 A1 | 8/2003 |
| WO | WO 2004/056827 A2 | 7/2004 |
| WO | WO 2004/060305 A2 | 7/2004 |
| WO | WO 2004/060305 A3 | 7/2004 |
| WO | WO 2004/060306 A2 | 7/2004 |
| WO | WO 2004/060306 A3 | 7/2004 |
| WO | WO 2004/061084 A2 | 7/2004 |
| WO | WO 2004/061084 A3 | 7/2004 |
| WO | WO 2004/089929 A1 | 10/2004 |
| WO | WO 2004/111009 A1 | 12/2004 |
| WO | WO 2005/014554 A1 | 2/2005 |
| WO | WO 2005/023761 A2 | 3/2005 |
| WO | WO 2005/023761 A3 | 3/2005 |
| WO | WO 2005/110994 | * 11/2005 |

OTHER PUBLICATIONS

Watt, A.P., et al., "Use of chiral liquid chromatography—tandom mass spectrometry to investigate the metabolism of racemic cholecystokinin-B antagonists," *J. Chromatogr. A* 896:217-227, Elsevier Science B.V. (2000).

Search results of STN CHEMCATS Database, May 15, 2006 (American Chemical Society).

P38 Drug Discovery Program, Locus Pharmaceuticals, Nov. 2, 2004.

Wilson, K.P., et al., "Crystal Structure of p38 Mitogen-activated Protein Kinase," *J. Biol. Chem.* 44:27696-27700, American Society for Biochemistry & Molecular Biology, Inc. (1996).

Co-pending U.S. Appl. No. 11/649,363, inventors Michelotti, E.L., et al., filed Jan. 4, 2007.

* cited by examiner

INHIBITORS OF PROTEIN KINASES

The application claims the benefit of U.S. Provisional Application No. 60/633,726, filed Dec. 7, 2004, which is herein incorporated by reference in its entirety.

BACKGROUND OF THE INVENTION

1. Field of the Invention

The present invention relates to compounds of Formula I that are useful as conformational modulators of a protein kinase. The compounds are also useful for inhibiting a protein kinase. The present invention also relates to a composition comprising said compound, and various methods of using a compound of Formula I to treat a protein kinase-mediated condition or inhibit a protein kinase.

2. Background Art

Protein kinases play a vital role in the functioning of cellular processes. The activation and deactivation of particular molecular pathways are often controlled by the phosphorylation or dephosphorylation of one or more proteins.

For example, mitogen activated protein kinases, such as p38 kinase, are activated in response to various stress stimuli, including, but not limited to, proinflammatory cytokines, endotoxin, ultraviolet light, and osmotic shock. Four isoforms of p38 have been described. The α and β forms are expressed in inflammatory cells and are considered to be key mediators of TNF-α production. Inhibition of the enzymes p38α and β in cells results in reduced levels of expression of TNF-α, and such inhibitors are effective in animal models of inflammatory disease.

Numerous small molecule inhibitors of p38 are known in the art. These compounds are thought to exert their effects by binding discrete locations on the surface of a p38 kinase. For example, certain p38 inhibitors block the production of TNF-α and IL-1; others can directly interfere with many of their secondary biological effects.

A protein can exist in a number of different conformations. These conformations can differ from each other in various ways. For example, the conformations can have different specific amino acids existing in various three-dimensional configurations. On a more global perspective, a protein can exist in different configurations of its overall tertiary structure. For example, certain proteins can exist in both an "open" conformation and a "closed" conformation.

A compound that can stabilize the open conformation of a protein kinase would be valuable as a tool for studying the action of kinases. Such a compound would also be useful for many reasons, for example, as a tool for drug discovery.

SUMMARY OF THE INVENTION

A first aspect of the present invention is directed to a compound of Formula I.

A second aspect of the present invention is directed to a composition comprising a compound of Formula I and a suitable carrier or excipient.

A third aspect of the present invention is directed to a method of inhibiting or modulating the activity of a protein kinase, comprising contacting the protein kinase with a compound of Formula I.

A fourth aspect of the present invention is directed to a method of identifying a conformation of a protein kinase, comprising forming a crystal of the protein kinase complexed with a compound of Formula I.

A fifth aspect of the present invention is directed to a method of identifying a compound that can bind to or inhibit a protein kinase.

A sixth aspect of the present invention is directed to a crystal structure of a protein kinase having an open conformation.

A seventh aspect of the present invention is directed to crystallized protein kinase complexed with a compound of Formula I.

DETAILED DESCRIPTION OF THE INVENTION

The present invention provides a compound that binds to a protein kinase and induces a conformational change in the protein, such that an allosteric site on the protein is made exposed and stabilized. The allosteric site is an area of the protein kinase to which a second compound can bind and affect the function of the protein. The display of this allosteric site is useful, for example, for identifying or designing a compound that can inhibit the protein kinase.

The compounds of the present invention are also useful, in certain embodiments, as inhibitors of a protein kinase. The compounds of the present invention in some embodiments are useful as inhibitors of one or more of the following kinases: DDR2, EphA1, EphA2, EphA3, EphA5, EphA7, EphA8, c-RAF, Flt1, Flt3, Hck, JNK2α2, JNK3α3, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAP-KAP-K2, PDGFR-beta, PKA, PKC-alpha, and Src. In another embodiment, the compound is an inhibitor of one or more of the following kinases: c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src. In another embodiment, a compound according to the invention is an inhibitor of one or more of the following kinases: c-RAF, Flt3, JNK3a3, JNK3, Lck, Lyn, p38α, p38γ, p38γ, p38δ, Tie2, and TrkB.

In still other embodiments, the compound of the present invention is useful in the treatment of protein kinase-mediated inflammatory and other disorders, including, but not limited to, bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, chronic obstructive pulmonary disorder, cardiac reperfusion injury, renal reperfusion injury, thrombus, glomerulonephritis, Crohn's disease, ulcerative colitis, inflammatory bowel disease, multiple sclerosis, endotoxin shock, osteoporosis, Alzheimer's disease, congestive heart failure, allergy, cancer, and cachexia.

A first aspect of the present invention is directed to a compound of Formula I:

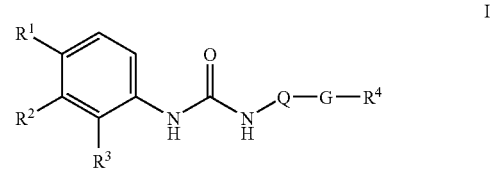

or a pharmaceutically acceptable salt thereof, wherein
$R^1$ is $R^5$—$L^1$ or $R^6$—$L^2$;

$R^2$ and $R^3$ are independently selected from the group consisting of hydrogen, $C_{1-6}$ alkyl, halogen, hydroxyl, $C_{1-6}$ alkoxy, $C_{1-6}$ haloalkyl, amino, $C_{1-6}$ alkylamino, and $C_{1-6}$ dialkylamino, or alternatively $R^2$ and $R^3$ together with the carbon atoms to which they are attached form a 5-8 membered ring;

$R^4$ is

or

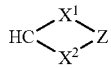

wherein $X^1$ and $X^2$ are independently $(CR^7R^8)_n$, wherein n is independently at each occurrence 1, 2, or 3, and wherein Z is —O—, —NH—, —HN—SO$_2$—, —NHC(O)—, —S—, —S(O)—, —SO$_2$—, or —C(O)—;

$R^5$ is a 5- or 6-membered aryl or heteroaryl ring containing 1, 2, 3, or 4 heteroatoms optionally substituted with one or more groups independently selected from the group consisting of halogen, alkyl, haloalkyl, hydroxyalkyl, alkoxyalkyl, amino, aminocarbonyl, $C_{1-6}$ alkylaminocarbonyl, $C_{1-6}$ dialkylaminocarbonyl, phenyl, and methoxyphenyl;

$L^1$ is —O—, —S—, —CH$_2$—, —OCH$_2$—, —CH$_2$O—, —SCH$_2$—, —CH$_2$S—, —CH(OH)—, —C(O)—, —CX$_2$—, or —CXH—, wherein X is a halogen;

$R^6$ is morpholinyl, thiomorpholinyl, tetrahydropyranyl, tetrahydrofuranyl, oxothiomorpholinyl, dioxothiomorpholinyl, piperazinyl, or piperidinyl; and $L^2$ is $(CR^9R^{10})_m$, wherein each occurrence of $R^9$ and $R^{10}$ is independently selected from the group consisting of H and $C_{1-4}$ alkyl, and m is 1, 2, or 3;

Q is a diradical of a 5-membered heteroaryl ring, each of which is optionally substituted with one or more of $R^{11}$ and $R^{12}$;

G is a linker of an optionally substituted $C_{1-3}$ alkylene, C=O, —C(O)NH—, or a single bond;

$R^7$ and $R^8$ are independently at each occurrence hydrogen, $C_{1-4}$ alkyl, halogen, hydroxyl, amino, $C_{1-4}$ alkylamino, aminocarbonyl, $C_{1-4}$ alkylaminocarbonyl, $C_{1-4}$ alkoxycarbonyl, hydroxymethyl, aminomethyl, $C_{1-4}$ alkylaminomethyl, and $C_{1-4}$ alkylaminocarbonylmethyl;

$R^{11}$ is independently $C_{3-10}$ alkyl or $C_{3-10}$ haloalkyl, each of which is optionally substituted with one to three phenyl groups; $C_{3-7}$ cycloalkyl, which is optionally substituted with one or more $C_{1-3}$ alkyl, halogen, hydroxy, oxo, or thioketo; $C_{3-10}$ optionally substituted cycloheteroalkyl; $C_{3-10}$ branched alkenyl which may optionally be partially or fully halogenated, and which is optionally substituted with one to three $C_{1-5}$ alkyl or a phenyl group; $C_{5-7}$ cycloalkenyl optionally substituted with one to three $C_{1-3}$ alkyl groups; cyano; or $C_{1-4}$ alkoxycarbonyl; and $R^{12}$ is $C_{1-5}$ alkyl, halogen, hydroxy, $C_{1-5}$ alkoxy, $C_{1-5}$ amino, $C_{1-5}$ alkylamino, $C_{1-5}$ dialkylamino, or optionally substituted phenyl.

In another embodiment, the present invention is directed to a compound of Formula I wherein $R^1$ is $R^5$—$L^1$ or $R^6$—$L^1$;

$R^2$ and $R^3$ are independently selected from the group consisting of hydrogen, $C_{1-6}$ alkyl, halogen, hydroxyl, $C_{1-6}$ alkoxy, $C_{1-6}$ haloalkyl, amino, $C_{1-6}$ alkylamino, and $C_{1-6}$ dialkylamino, or alternatively $R^2$ and $R^3$ together with the carbon atoms to which they are attached form a 5-8 membered ring;

$R^4$ is

or

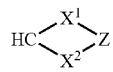

wherein $X^1$ and $X^2$ are independently $(CR^7R^8)_n$, wherein n is independently at each occurrence 1, 2, or 3, and wherein Z is —O—, —NH—, —HN—SO$_2$—, —NHC(O)—, —S—, —S(O)—, —SO$_2$—, or —C(O)—;

$R^5$ is a 5 or 6-membered aryl or heteroaryl ring containing 1, 2, or 3 nitrogen atoms optionally substituted with one or more groups independently selected from the group consisting of halogen, alkyl, haloalkyl, hydroxyalkyl, alkoxyalkyl, aminocarbonyl, $C_{1-6}$ alkylaminocarbonyl, and $C_{1-6}$ dialkylaminocarbonyl;

$L^1$ is —O—, —S—, —CH$_2$—, —OCH$_2$—, —CH$_2$O—, —SCH$_2$—, —CH$_2$S—, —CH(OH)—, —C(O)—, —CX$_2$—, or —CXH—, wherein X is a halogen;

$R^6$ is morpholinyl, thiomorpholinyl, tetrahydropyranyl, tetrahydrofuranyl, oxothiomorpholinyl, dioxothiomorpholinyl, piperazinyl, or piperidinyl; and $L^2$ is $(CR^9R^{10})_m$, wherein each occurrence of $R^9$ and $R^{10}$ is independently selected from the group consisting of H and $C_{1-4}$ alkyl, and m is 1, 2, or 3;

Q is a diradical of 5-membered heteroaryl optionally substituted with one or more of $R^{11}$ and $R^{12}$;

G is a linker of an optionally substituted $C_{1-3}$ alkylene, C=O or a single bond;

$R^7$ and $R^8$ are independently at each occurrence hydrogen, $C_{1-4}$ alkyl, halogen, hydroxyl, amino, $C_{1-4}$ alkylamino, aminocarbonyl, $C_{1-4}$ alkylaminocarbonyl, $C_{1-4}$ alkoxycarbonyl, hydroxymethyl, aminomethyl, $C_{1-4}$ alkylaminomethyl, and $C_{1-4}$ alkylaminocarbonylmethyl;

$R^{11}$ is independently $C_{3-10}$ alkyl or $C_{3-10}$ haloalkyl, each of which is optionally substituted with one to three phenyl groups; $C_{3-7}$ cycloalkyl, which is optionally substituted with one or more $C_{1-3}$ alkyl, halogen, hydroxy, oxo, or thioketo; $C_{3-10}$ optionally substituted cycloheteroalkyl; $C_{3-10}$ branched alkenyl which may optionally be partially or fully halogenated, and which is optionally substituted with one to three $C_{1-5}$ alkyl or a phenyl group; $C_{5-7}$ cycloalkenyl optionally substituted with one to three $C_{1-3}$ alkyl groups; cyano; or $C_{1-4}$ alkoxycarbonyl; and $R^{12}$ is $C_{1-5}$ alkyl, halogen, hydroxy, $C_{1-5}$ alkoxy, $C_{1-5}$ amino, $C_{1-5}$alkylamino, $C_{1-5}$ dialkylamino, or optionally substituted phenyl.

In one embodiment, the present invention is directed to a compound of Formula I, wherein $R^1$ is $R^5$—$L^1$. In another embodiment, $R^1$ is $R^6$—$L^2$.

In one embodiment, $L^1$ is —$CH_2$—. In another embodiment, $L^1$ is —O—. In other embodiments, $L^1$ is selected from the group consisting of —CH(OH)—, —C(O)—, —CHX—, and —$CX_2$—.

In one embodiment, $L^2$ is methylene, ethylene, or propylene. In another embodiment, $L^2$ together with its substituents is a $C_{3-6}$ branched alkylene linker.

In one embodiment, $R^1$ is 4-pyridyloxy or 3-pyridyloxy, each of which is optionally substituted.

In one embodiment, $R^2$ and $R^3$ are independently selected from the group consisting of hydrogen, $C_{1-6}$ alkyl, halogen, hydroxyl, $C_{1-6}$ alkoxy, $C_{1-6}$ haloalkyl, amino, $C_{1-6}$ alkylamino, and $C_{1-6}$ dialkylamino. Suitable $R^2$ and $R^3$ groups include but are not limited to hydrogen, methyl, ethyl, propyl, chloro, bromo, hydroxyl, methoxy, ethoxy, propoxy, chloroethoxy, dichloroethoxy, amino, methylamino, ethylamino, butylamino, dimethylamino, methylethylamino, and diisopropylamino. In another embodiment, $R^2$ and $R^3$ are both hydrogen.

In another embodiment, $R^2$ and $R^3$ together form a ring, wherein said ring is fused with the phenyl ring thereby forming a bicyclic ring system. Suitable rings include a carbocyclic, heterocyclic, aryl ring, nonaromatic ring, heteroaryl ring, and the like. In other embodiments, $R^2$ and $R^3$ form a 3-6 membered ring. For example, in one embodiment, $R^2$, $R^3$, and the phenyl ring together form a naphthyl ring. Other suitable ring systems formed by $R^2$ and $R^3$ include tetrahydronaphthyl, quinolinyl, isoquinolinyl, and the like.

In another embodiment, Q can be pyrrole, pyrazole, imidazole, oxazole, thiazole, furan, or thiophene diradical, each of which is optionally substituted with one or more of $R^{11}$ and $R^{12}$. For example, in each of the above embodiments, Q is selected from the group consisting of thienyl, pyrazolyl, and thiazolyl, each of which is optionally substituted with one or more of $R^{11}$ and $R^{12}$. In certain embodiments, the 5-membered heterocycle is substituted with a $C_{1-5}$ alkyl group, preferably a tert-butyl group. Other substituents include, but are not limited to methyl, ethyl, and isopropyl. In another embodiment, Q is optionally substituted thienyl, such as substituted in the 5-position with a $C_{1-5}$ alkyl group.

In other embodiments, Q is a thienyl group in which the urea is bonded to the 2 position and G is bonded to the three position. Alternatively, Q is a thienyl group in which the urea is bonded to the 3 position and G is bonded to the 2 position.

In another embodiment, Q is a pyrazolyl substituted with a $C_{1-5}$ alkyl group.

In one embodiment, G is a linker of an optionally substituted methylene, ethylene, or propylene linker. In another embodiment, G is —$CH_2$—, —$CH_2CH_2$—, or —$CH_2CH_2CH_2$—. In an alternative embodiment, G is a single bond. In another embodiment, G is —C(O)—.

In one embodiment, $R^4$ is

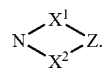

In another embodiment, $R^4$ is

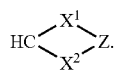

In other suitable embodiments, $X^1$ and $X^2$ are both unsubstituted $C_{1-3}$ alkylene groups. In other embodiments, $X^1$ and $X^2$ are both unsubstituted ethylene. In certain embodiments, Z is selected from the group consisting of —NHC(O)—, —S(O)— and —NHS(O)—.

Suitable values of $R^4$ include morpholinyl, thiomorpholinyl, oxothiomorpholinyl, dioxothiomorpholinyl, oxopiperazinyl, oxodiazepanyl, and dioxothiadiazepanyl. Other suitable groups include, but are not limited to, 1-oxothiomorpholinyl, 1,1-dioxothiomorpholinyl, 4-morpholinyl, 3-oxopiperazinyl, 5-oxo-1,4-diazepanyl, and 1,1-dioxo[1,2,5]thiadiazepanyl.

Other suitable $R^4$ groups include:

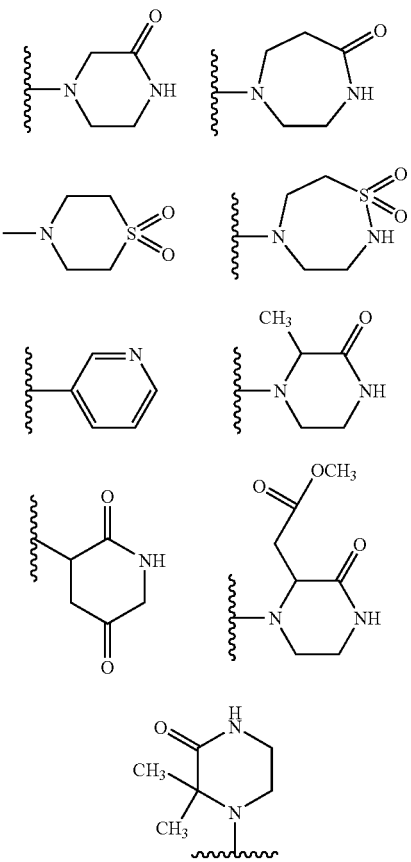

Other suitable $R^4$ groups include:

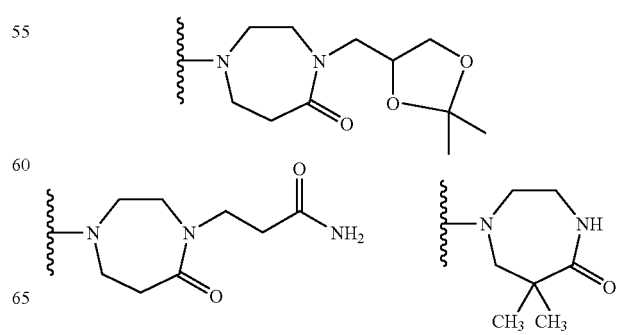

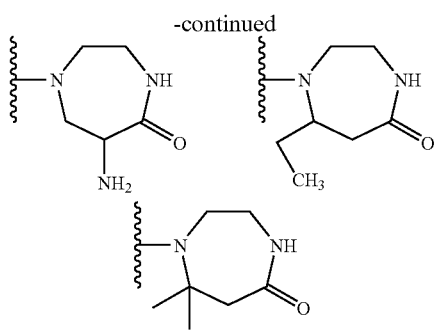

Other suitable R⁴ groups include:

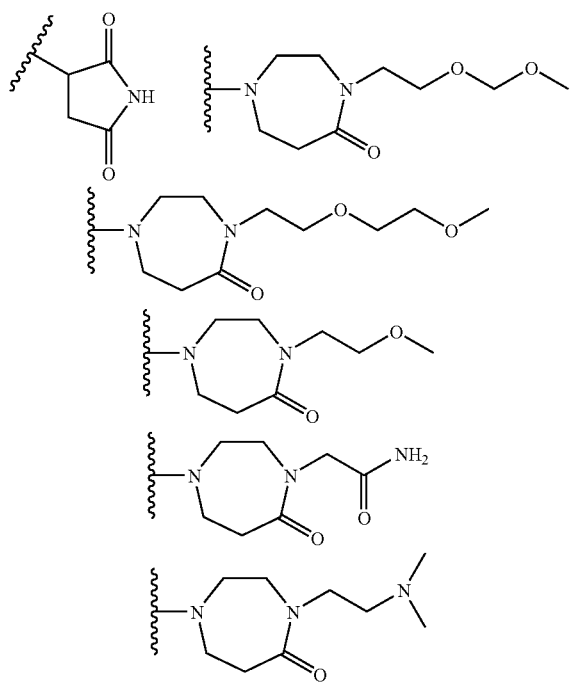

In another embodiment, $R^5$ is a 5 or 6-membered heteroaryl ring containing 1, 2, 3, or 4 heteroatoms optionally substituted as described above. For example, $R^5$ can be a 5 or 6-membered ring containing 1 or 2 nitrogen atoms and can be substituted by halogen, alkyl, haloalkyl, hydroxyalkyl, alkoxyalkyl, amino, aminocarbonyl, $C_{1-6}$ alkylaminocarbonyl, or $C_{1-6}$ dialkylaminocarbonyl. Alternatively, $R^5$ is an optionally substituted phenyl ring.

In one embodiment, $R^5$ is a 6-membered ring containing 1, 2, or 3 nitrogen atoms. The 6-membered ring can be optionally substituted with one or more substituents selected from the group consisting of halogen, alkyl, haloalkyl, hydroxyalkyl, and alkoxyalkyl. In other specific embodiments, $R^5$ is a pyridyl group, such as a 2-pyridyl, 3-pyridyl, or 4-pyridyl.

In another embodiment, $R^5$ is a 9-membered bicyclic heteroaryl ring containing 1, 2, or 3 heteroatoms, such as nitrogen, sulfur, and oxygen, and combinations thereof. The heteroaryl ring can be optionally substituted with one or more substituents selected from the group consisting of amino, aminocarbonyl, $C_{1-6}$ alkylaminocarbonyl, and $C_{1-6}$ dialkylaminocarbonyl.

Other suitable $R^5$ groups include 2-(methylcarbamoyl)pyridin-4-yl, 3,5-dichloropyridin-4-yl, phenyl, and 3,4-difluorophenyl.

In another embodiment, $R^6$ is morpholinyl or thiomorpholinyl. Alternatively, $R^6$ is tetrahydropyranyl or tetrahydrofuranyl. In other embodiments, $R^6$ is oxothiomorpholinyl, dioxothiomorpholinyl, piperazinyl, or piperidinyl. Each of the $R^6$ groups may be optionally substituted. In certain embodiments, the $R^6$ group is optionally substituted with 1, 2, or 3 substituents independently selected from the group consisting of methyl, ethyl, and propyl.

In another embodiment, $L^1$ is O, S, or —CH₂—. In another embodiment, $L^1$ is —SCH₂— or —CH₂S—. In another embodiment, $L^1$ is —CH(OH)— or —C(O)—. In a further embodiment, $L^1$ is —CX₂—, or —CXH—, wherein X is a halogen. In another embodiment, $L^1$ is a single bond.

In another embodiment, $L^2$ is $(CR^9R^{10})_m$, wherein each occurrence of $R^5$ and $R^6$ is hydrogen and m is 1, 2, or 3. In another embodiment, $L^2$ is methylene, ethylene, or propylene substituted with a $C_{1-4}$ alkyl group. In another embodiment, $L^2$ is a methylene linker.

Another embodiment of the invention is directed to a compound of Formula I wherein Z is S, S(O), or S(O)₂; and $X^1$ and $X^2$ are both unsubstituted ethylene.

In another embodiment, Q, together with G and $R^4$, forms a group selected from the following:

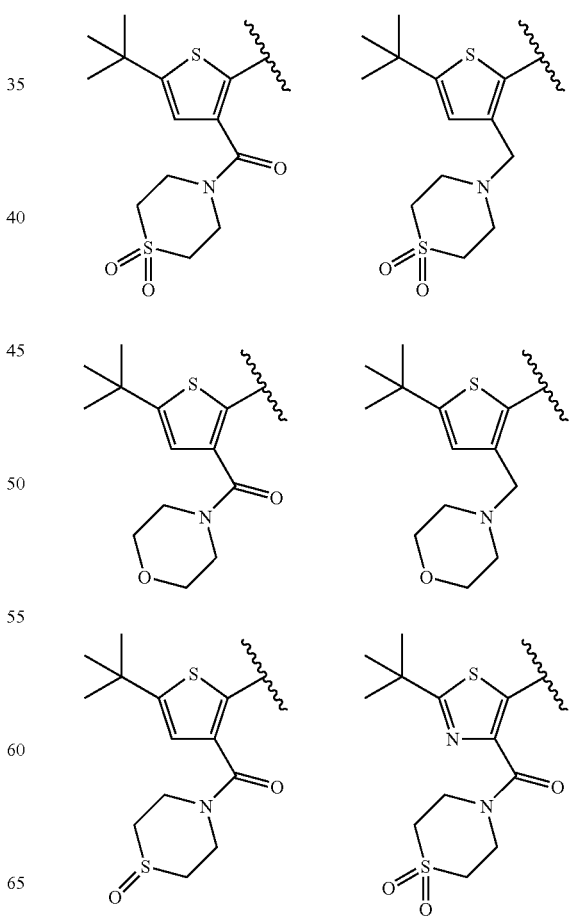

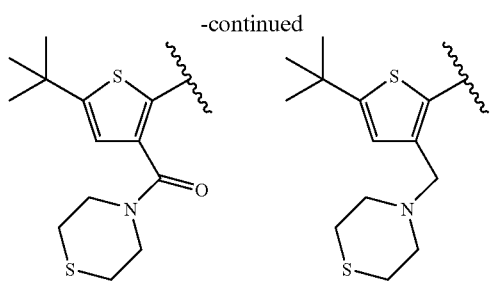
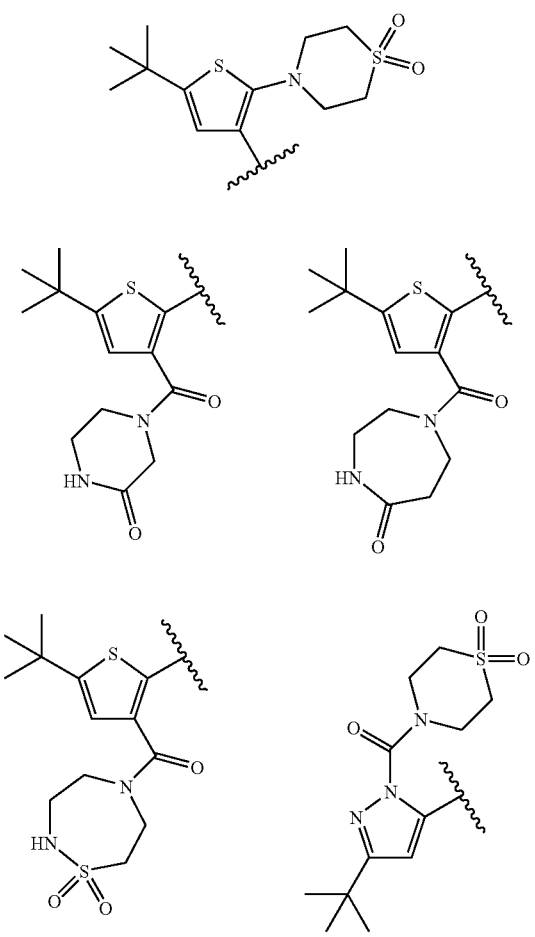
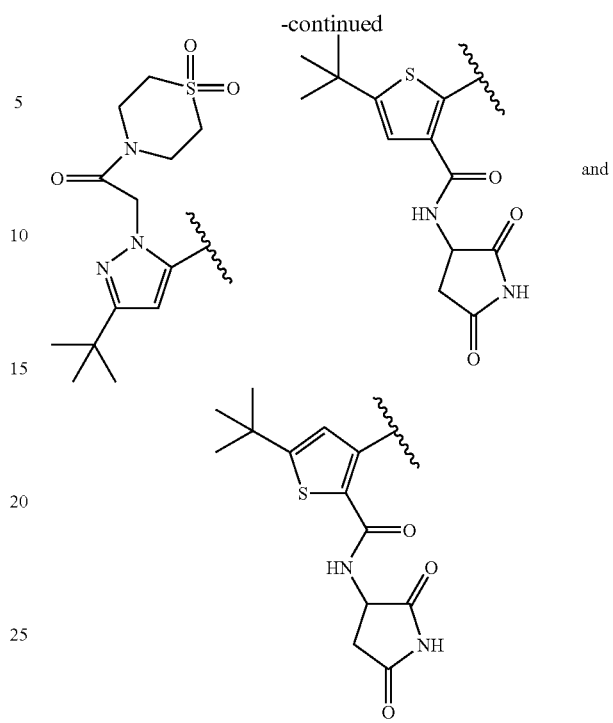

In another embodiment, $R^7$ and $R^8$ are independently selected from the group consisting of hydrogen, $C_{1-4}$ alkyl, halogen, amino, $C_{1-4}$ alkylamino, aminocarbonyl, $C_{1-4}$ alkylaminocarbonyl, and $C_{1-4}$ alkoxycarbonyl. In other embodiments, suitable values of $R^7$ and $R^8$ include hydrogen, methyl, ethyl, isopropyl, chloro, fluoro, amino, methylamino, ethylamino, hydroxy, propylamino, methylaminocarbonyl, methoxycarbonyl, and ethoxycarbonyl.

In another embodiment, $R^9$ and $R^{10}$ are independently selected from the group consisting of hydrogen, methyl, ethyl, and propyl. In another embodiment, $R^9$ and $R^{10}$ are independently selected from the group consisting of hydrogen, methyl, and ethyl.

In another embodiment, $R^{11}$ is selected from the group consisting of $C_{3-10}$ alkyl and $C_{3-10}$ haloalkyl. In another embodiment, $R^{11}$ is $C_{3-7}$ cycloalkyl, optionally substituted with one or more $C_{1-3}$ alkyl, halogen, hydroxy, oxo, or thioketo. In another embodiment, $R^{11}$ is $C_{3-10}$ optionally substituted cycloheteroalkyl. In yet another embodiment, $R^{11}$ is selected from the group consisting of $C_{3-10}$ branched alkenyl and $C_{3-10}$ branched haloalkenyl, each of which is optionally substituted with one to three $C_{1-5}$ alkyl groups. In yet another embodiment, $R^{11}$ is selected from the group consisting of $C_{5-7}$ cycloalkenyl optionally substituted with one to three $C_{1-3}$ alkyl groups; cyano; and $C_{1-4}$ alkoxycarbonyl. Suitable values of $R^{11}$ include but are not limited to propyl, butyl, hexyl, chlorobutyl, cyclopropyl, cyclohexyl, cyclohexanonyl, and the like.

In another embodiment, $R^{12}$ is selected from the group consisting of $C_{1-5}$ alkyl, halogen, hydroxy, $C_{1-5}$ alkoxy, amino, $C_{1-5}$ alkylamino, and $C_{1-5}$ dialkylamino. In another embodiment, $R^{12}$ is selected from the group consisting of phenyl and substituted phenyl. Suitable values of $R^{12}$ include but are not limited to methyl, ethyl, butyl, fluoro, bromo, hydroxyl, methoxy, ethoxy, propoxy, amino, methylamino, ethylamino, butylamino, diisopropylamino, and phenyl.

A first subclass of compounds falling within the scope of the present invention includes compounds of Formula I wherein $R^1$ is optionally substituted pyridyloxy; and Q is optionally substituted thienyl.

In one embodiment within this first subclass of compounds, $R^1$ is 4-pyridyloxy having one or two substituents selected from the group consisting of $C_{1-5}$ alkyl, $C_{1-5}$ alkoxy, hydroxyl, amino, $C_{1-5}$ alkylamino, $C_{1-5}$ dialkylamino, cyano, halogen, carboxy, aminocarbonyl, and $C_{1-5}$ alkoxycarbonyl. In another embodiment of this first subclass, $R^1$ unsubstituted 4-pyridyloxy.

In another embodiment within this first subclass, Q is unsubstituted thienyl. In certain embodiments, the thienyl group is bonded to N of the urea in the 2 or 3 position. In other embodiments, the thienyl group is substituted in the 5-position with a $C_{1-5}$ alkyl group, for example a tert-butyl group.

In another embodiment within this first subclass, $R^4$ is a group selected from the group consisting of morpholin-4-yl, thiomorpholin-4-yl, 1-oxothiomorpholin-4-yl, and 1,1-dioxothiomorpholin-4-yl, each of which is optionally substituted.

In another embodiment within this first subclass, G is selected from the group consisting of $CH_2$, $CH_2CH_2$, $C(O)$, and $CH_2C(O)$.

A second subclass of compounds falling within the scope of the present invention includes compounds of Formula I wherein $R^1$ is optionally substituted pyridyloxy; and $R^4$ is a group selected from the group consisting of morpholin-4-yl, thiomorpholin-4-yl, 1-oxothiomorpholin-4-yl, and 1,1-dioxothiomorpholin-4-yl, each of which is optionally substituted.

A third subclass of compounds falling within the scope of the present invention includes compounds of Formula I, wherein $R^1$ is optionally substituted pyridyloxy; and G is selected from the group consisting of $CH_2$ and $C(O)$. Within this third subclass, another embodiment includes those compounds wherein $R^2$ and $R^3$ are hydrogen.

In another embodiment, the present invention is directed to a compound according to Formula I, having one of the formulas:

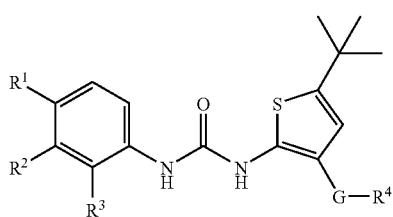

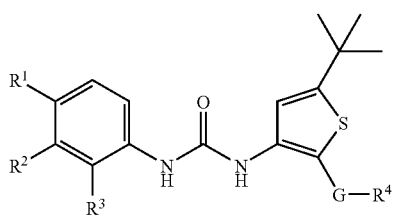

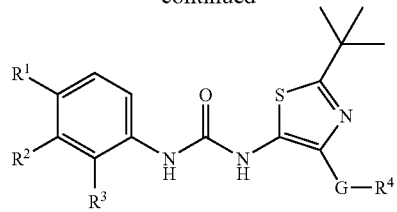

wherein $R^1$, $R^2$, $R^3$, G, and $R^4$ are as defined above.

Other embodiments of the invention include a compound according to Formula I wherein $R^1$ is a 3,5-dichloropyridin-4-yloxy group and G and $R^4$ together form a thiomorpholine-1,1-dioxide-4-carbonyl group;

$R^1$ is a 2-(methylcarbamoyl)pyridin-4-yloxy group and G and $R^4$ together form a morpholine-4-carbonyl)thiophen-2-yl group;

$R^1$ is a pyridin-4-ylmethyl group and G and $R^4$ together form a thiomorpholine-1,1-dioxide-4-carbonyl group;

$R^1$ is a 2-(methylcarbamoyl)pyridin-4-yloxy group and G and $R^4$ together form a thiomorpholine-1,1-dioxide-4-carbonyl)thiazol-5-yl group;

$R^1$ is a pyridin-4-yloxy group G and $R^4$ together form a 5-oxo-1,4-diazepane-1-carbonyl)thiophen-3-yl group;

$R^1$ is a pyridin-4-yloxy group G and $R^4$ together form a 1,2,5-thiadiazepane-1,1-dioxide-5-carbonyl group;

$R^1$ is a pyridin-4-yloxy group G and $R^4$ together form a 2-oxopiperazine-4-carbonyl group;

$R^1$ is a pyridin-4-yloxy group G and $R^4$ together form a thiomorpholine-1,1-dioxide-4-carbonyl group;

$R^1$ is a pyridin-4-yloxy group G and $R^4$ together form a thiomorpholine-1-oxide-4-carbonyl group;

$R^1$ is a pyridin-4-yloxy group G and $R^4$ together form a thiomorpholine-1,1-dioxide-4-carbonyl group;

$R^1$ is a pyridin-4-yloxy group G and $R^4$ together form a thiomorpholine-1,1-dioxide-4-carbonyl group;

$R^1$ is a 2-(methylcarbamoyl)pyridin-4-yloxy group and G and $R^4$ together form a 1,2,5-thiadiazepane-1,1-dioxide-5-carbonyl)thiophen-3-yl group;

$R^1$ is a 2-(methylcarbamoyl)pyridin-4-yloxy group and $R^4$ together form a 5-oxo-1,4-diazepane-1-carbonyl group;

$R^1$ is a 2-(methylcarbamoyl)pyridin-4-yloxy group and $R^4$ together form a 2-oxopiperazine-4-carbonyl group;

$R^1$ is a pyridin-4-yloxy group and G and $R^4$ together form a morpholine-4-carbonyl)thiophen-2-yl group;

$R^1$ is a pyridin-4-yloxy group and G and $R^4$ together form a thiomorpholine-4-carbonyl group;

$R^1$ is a 2-(methylcarbamoyl)pyridin-4-yloxy group and G and $R^4$ together form a thiomorpholine-1,1-dioxide-4-carbonyl group;

$R^1$ is a 2-(methylcarbamoyl)pyridin-4-yloxy group and G and $R^4$ together form a 2-oxopiperazine-4-carbonyl group;

$R^1$ is a 2-(methylcarbamoyl)pyridin-4-yloxy and G and $R^4$ together form a 5-oxo-1,4-diazepane-1-carbonyl group;

$R^1$ is a 2-(methylcarbamoyl)pyridin-4-yloxy group and G and $R^4$ together form a 1,2,5-thiadiazepane-1,1-dioxide-5-carbonyl group; and $R^1$ is a 2-(methylcarbamoyl)pyridin-4-yloxy and group G and $R^4$ together form a thiomorpholine-1,1-dioxide-4-carbonyl group; and wherein any of the preceding subgroups may be optionally substituted.

In another embodiment, the present invention is directed to a compound of Formula I having an inhibitory effect on a protein kinase of at least 60%, 70%, 80%, 90%, or 95% at a concentration of 2 µM, as determined according to an assay described herein. The present invention is also directed to a compound of any one of the subclasses of compounds described above, wherein the compound has an inhibitory effect on a protein kinase of at least 60%, 70%, 80%, 90%, or 95% at a concentration of 2 µM, as determined according to an assay described herein. In one embodiment, the invention is also directed to a compound of any one of the subclasses of compounds described above, wherein the compound has an inhibitory effect on a protein kinase of at least 60%, 70%, 80%, 90%, or 95% at a concentration of 2 µM, wherein said kinase is serine-threonine kinase. In alternative embodiment, the invention is also directed to a compound of any one of the subclasses of compounds described above, wherein the compound has an inhibitory effect on a protein kinase of at least 60%, 70%, 80%, 90%, or 95% at a concentration of 2 µM, wherein said kinase is tyrosine kinase. In another embodiment, the invention is also directed to a compound of any one of the subclasses of compounds described above, wherein the compound has an inhibitory effect on a protein kinase of at least 60%, 70%, 80%, 90%, or 95% at a concentration of 2 µM, wherein said kinase is mitogen activated protein kinase.

By way of a non-limiting example, one embodiment of the invention is directed to a compound of Formula I wherein $R^1$ is 4-pyridyloxy; and Q is optionally substituted thienyl; and wherein said compound inhibits a protein kinase by at least 80% at a concentration of 2 µM, wherein said protein kinase is selected from the group consisting of DDR2, EphA1, EphA2, EphA3, EphA5, EphA7, EphA8, c-RAF, Flt1, Flt3, Hck, JNK2α2, JNK3α3, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAP-KAP-K2, PDGFR-beta, PKA, PKC-alpha, and Src. In another embodiment, the protein kinase is selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

In another embodiment, the present invention is directed to a compound according to Formula I wherein $R^1$ is pyridyloxy optionally substituted with 1-3 of $C_{1-4}$ alkyl, halogen, amino, hydroxy, cyano, $C_{1-4}$ haloalkyl, and $C_{1-4}$ alkoxy; and wherein said compound inhibits a protein kinase by at least 75% at a concentration of 2 µM, wherein said protein kinase is selected from the group consisting of c-RAF, Flt3, JNK3a3, JNK3, Lck, Lyn, p38α, p38β, p38γ, p38δ, Tie2, and TrkB.

In another embodiment, the present invention is directed to a compound according to Formula I wherein $R^1$ is pyridyloxy optionally substituted with 1-3 of $C_{1-4}$ alkyl, halogen, amino, hydroxy, cyano, $C_{1-4}$ haloalkyl, and $C_{1-4}$ alkoxy; and wherein said compound inhibits a protein kinase by at least 75% at a concentration of 2 µM.

Examples of suitable compounds, which are useful in the methods and compositions disclosed herein, include:

1-[5-tert-butyl-3-(1,1-dioxo-1$\lambda^{6[}$1,2,5]thiadiazepane-5-carbonyl)thiophen-2-yl]-3-[4-(pyridin-4-yloxy)phenyl]urea;

1-[5-tert-butyl-3-(3-oxo-piperazine-1-carbonyl)thiophen-2-yl]-3-[4-(pyridin-4-yloxy)phenyl]urea;

1-[5-tert-butyl-3-(1,1-dioxo-1$\lambda^6$-thiomorpholine-4-carbonyl)thiophen-2-yl]-3-[4-(pyridin-4-yloxy)phenyl]urea;

1-[5-tert-butyl-3-(5-oxo-[1,4]diazepane-1-carbonyl)thiophen-2-yl]-3-[4-(pyridin-4-yloxy)phenyl]urea; 1-(5-tert-Butyl-3-(thiomorpholine-1,1-dioxide-4-carbonyl)thiophen-2-yl)-3-(4-(2-(methylcarbamoyl)pyridin-4-yloxy)phenyl)urea;

1-(5-tert-Butyl-3-(1,2,5-thiadiazepane-1,1-dioxide-5-carbonyl)thiophen-2-yl)-3-(4-(2-(methylcarbamoyl)pyridin-4-yloxy)phenyl)urea;

1-(5-tert-Butyl-3-(5-oxo-1,4-diazepane-1-carbonyl)thiophen-2-yl)-3-(4-(2-(methylcarbamoyl)pyridin-4-yloxy)phenyl)urea;

1-(5-tert-Butyl-3-(2-oxopiperazine-4-carbonyl)thiophen-2-yl)-3-(4-(2-(methylcarbamoyl)pyridin-4-yloxy)phenyl)urea;

1-(5-tert-Butyl-2-(thiomorpholine-1,1-dioxide-4-carbonyl)thiophen-3-yl)-3-(4-(2-(methylcarbamoyl)pyridin-4-yloxy)phenyl)urea;

1-(5-tert-Butyl-3-(thiomorpholine-4-carbonyl)thiophen-2-yl)-3-(4-(pyridin-4-yloxy)phenyl)urea;

1-(5-tert-Butyl-3-(morpholine-4-carbonyl)thiophen-2-yl)-3-(4-(pyridin-4-yloxy)phenyl)urea;

1-(5-tert-Butyl-2-(2-oxopiperazine-4-carbonyl)thiophen-3-yl)-3-(4-(2-(methylcarbamoyl)pyridin-4-yloxy)phenyl)urea;

1-(5-tert-Butyl-2-(5-oxo-1,4-diazepane-1-carbonyl)thiophen-3-yl)-3-(4-(2-(methylcarbamoyl)pyridin-4-yloxy)phenyl)urea;

1-(5-tert-Butyl-2-(1,2,5-thiadiazepane-1,1-dioxide-5-carbonyl)thiophen-3-yl)-3-(4-(2-(methylcarbamoyl)pyridin-4-yloxy)phenyl)urea;

1-(5-tert-Butyl-3-(thiomorpholine-1,1-dioxide-4-carbonyl)thiophen-2-yl)-3-(4-(pyridin-4-ylmethoxy)phenyl)urea;

1-(2-tert-Butyl-4-(thiomorpholine-1,1-dioxide-4-carbonyl)thiazol-5-yl)-3-(4-(pyridin-4-yloxy)phenyl)urea;

1-(5-tert-Butyl-3-(thiomorpholine-1-oxide-4-carbonyl)thiophen-2-yl)-3-(4-(pyridin-4-yloxy)phenyl)urea;

1-(5-tert-Butyl-2-(thiomorpholine-1,1-dioxide-4-carbonyl)thiophen-3-yl)-3-(4-(pyridin-4-yloxy)phenyl)urea;

1-(5-tert-Butyl-2-(2-oxopiperazine-4-carbonyl)thiophen-3-yl)-3-(4-(pyridin-4-yloxy)phenyl)urea;

1-(5-tert-Butyl-2-(1,2,5-thiadiazepane-1,1-dioxide-5-carbonyl)thiophen-3-yl)-3-(4-(pyridin-4-yloxy)phenyl)urea;

1-(5-tert-Butyl-2-(5-oxo-1,4-diazepane-1-carbonyl)thiophen-3-yl)-3-(4-(pyridin-4-yloxy)phenyl)urea;

1-(5-tert-Butyl-3-(thiomorpholine-1,1-dioxide-4-carbonyl)thiophen-2-yl)-3-(4-(3,5-dichloropyridin-4-yloxy)phenyl)urea;

1-(5-tert-Butyl-3-(morpholine-4-carbonyl)thiophen-2-yl)-3-(4-(2-(methylcarbamoyl)pyridin-4-yloxy)phenyl)urea;

1-(5-tert-Butyl-3-(thiomorpholine-1,1-dioxide-4-carbonyl)thiophen-2-yl)-3-(4-(pyridin-4-ylmethyl)phenyl)urea;

1-(2-tert-Butyl-4-(thiomorpholine-1,1-dioxide-4-carbonyl)thiazol-5-yl)-3-(4-(2-(methylcarbamoyl)pyridin-4-yloxy)phenyl)urea; and pharmaceutically acceptable salts thereof.

The present invention also includes a salt of a compound according to Formula I. The term salt refers to an acid- and/or base-addition salt of a compound according to Formula I. Acid-addition salts can be formed by adding an appropriate acid to the compound according to Formula I. Base-addition salts can be formed by adding an appropriate base to the compound according to Formula I. Said acid or base does not substantially degrade, decompose, or destroy said compound according to Formula I. Examples of suitable salts include hydrochloride, hydrobromide, acetate, fumarate, maleate, oxalate, and succinate salts. Other suitable salts include sodium, potassium, carbonate, and tromethamine salts.

It is also to be understood that the present invention is considered to encompass stereoisomers as well as optical isomers, e.g., mixtures of enantiomers as well as individual enantiomers and diastereomers, which arise as a consequence of structural asymmetry in selected compounds of the present series.

The compounds of Formula I may also be solvated, including hydrated. Hydration may occur during manufacturing of the compounds or compositions comprising the compounds, or the hydration may occur over time due to the hygroscopic nature of the compounds.

Certain compounds within the scope of Formula I may be derivatives referred to as "prodrugs." The expression "prodrug" denotes a derivative of a known direct acting drug, which derivative has enhanced delivery characteristics and therapeutic value as compared to the drug, and is transformed into the active drug by an enzymatic or chemical process. Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases, it is desirable to prepare double ester type prodrugs such as (acyloxy) alkyl esters or ((alkoxycarbonyl)oxy)alkyl esters.

When any variable occurs more than one time in any constituent or in Formula I, its definition on each occurrence is independent of its definition at every other occurrence, unless otherwise indicated. Also, combinations of substituents and/or variables are permissible only if such combinations result in stable compounds.

The term "alkyl," as used herein by itself or as part of another group, refers to both straight and branched chain radicals of up to 10 carbons, unless the chain length is otherwise limited, such as methyl, ethyl, propyl, isopropyl, butyl, 1-methylpropyl, 2-methylpropyl, pentyl, 1-methylbutyl, isobutyl, pentyl, t-amyl ($CH_3CH_2(CH_3)_2C-$), hexyl, isohexyl, heptyl, octyl, or decyl.

The term "alkenyl," as used herein by itself or as part of another group, refers to a straight or branched chain radical of 2-10 carbon atoms, unless the chain length is otherwise limited, including, but not limited to, ethenyl, 1-propenyl, 2-propenyl, 2-methyl-1-propenyl, 1-butenyl, 2-butenyl, 3-butenyl, pentenyl, 1-hexenyl, and 2-hexenyl.

The term "alkynyl," as used herein by itself or as part of another group, refers to a straight or branched chain radical of 2-10 carbon atoms, unless the chain length is otherwise limited, wherein there is at least one triple bond between two of the carbon atoms in the chain, including, but not limited to, ethynyl, 1-propynyl, 2-propynyl, 1-butynyl, 2-butynyl, 1-methyl-2-butynyl, 1-methyl-3-butynyl, 2-methyl-3-pentynyl, hexynyl, and heptynyl.

In instances herein where there is an alkenyl or alkynyl moiety as a substituent group, the unsaturated linkage, i.e., the vinylenyl or acetylenyl linkage, is preferably not directly attached to a nitrogen, oxygen or sulfur moiety.

The term "cycloalkyl," as used herein by itself or as part of another group, refers to cycloalkyl groups containing 3 to 14, preferably 3 to 10, carbon atoms. Typical examples are cyclopropyl, cyclobutyl, cyclopentyl, cyclohexyl, and bicyclo [2.2.2]octyl.

The term "cycloalkenyl," as used herein by itself or as part of another group, refers to cycloalkenyl groups containing 3 to 14, preferably 3 to 10, carbon atoms and 1 to 3 carbon-carbon double bonds. Typical examples include cyclopropenyl, cyclobutenyl, cyclopentenyl, cyclohexenyl, cycloheptenyl, and cyclohexdienyl.

The term "alkylene," as used herein by itself or as a part of another group, refers to a diradical of an unbranched saturated hydrocarbon chain, having, unless otherwise indicated, from 1 to 15 carbon atoms, preferably 1 to 10 carbon atoms and more preferably 1 to 6 carbon atoms. This term is exemplified by groups such as methylene ($-CH_2-$), ethylene ($-CH_2CH_2-$), propylene ($-CH_2CH_2CH_2-$), butylene, and the like.

The term "alkenylene," as used herein by itself or part of another group, refers to a diradical of an unbranched, unsaturated hydrocarbon chain, having, unless otherwise indicated, from 2 to 15 carbon atoms, preferably 1 to 10 carbon atoms, more preferably 2 to 6 carbon atoms, and having at least 1 and preferably from 1 to 6 sites of vinyl unsaturation. This term is exemplified by groups such as ethenylene ($-CH=CH-$), propenylene ($-CH_2CH=CH-$, $-CH=CHCH_2-$), and the like.

The term "alkoxy," as used herein by itself or as part of another group, refers to any of the above alkyl groups linked to an oxygen atom. Typical examples are methoxy, ethoxy, isopropyloxy, sec-butyloxy, and t-butyloxy.

The term "alkenyloxy," as used herein by itself or as part of another group, refers to any of the above alkenyl groups linked to an oxygen atom. Typical examples include ethenyloxy, propenyloxy, butenyloxy, pentenyloxy, and hexenyloxy.

The term "aryl," as used herein by itself or as part of another group, refers to monocyclic or bicyclic aromatic groups containing from 6 to 14 carbons in the ring portion, preferably 6-10 carbons in the ring portion. Typical examples include phenyl, naphthyl, anthracenyl, or fluorenyl.

The term "aralkyl" or "arylalkyl," as employed herein by itself or as part of another group, refers to $C_{1-6}$ alkyl groups as defined above having an aryl substituent, such as benzyl, phenylethyl, or 2-naphthylmethyl.

The term "heteroaryl," as used herein as used herein by itself or as part of another group, refers to groups having 5 to 14 ring atoms; 6, 10, or 14 π electrons shared in a cyclic array; and containing carbon atoms and 1, 2, 3, or 4 oxygen, nitrogen, or sulfur atoms. Examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups. Further heteroaryls are described in A. R. Katritzky and C. W. Rees, eds., Comprehensive Heterocyclic Chemistry The Structure, Reactions, Synthesis and Use of Heterocyclic Compounds, Vol. 1-8, Pergamon Press, NY (1984).

The term "alkylenedioxy," as used herein by itself or as part of another group, refers to a ring containing an alkylene group and two oxygen atoms, and is especially $C_{1-4}$ alkylenedioxy. Alkylenedioxy groups may optionally be substituted with halogen (especially fluorine). Typical examples include methylenedioxy (—$OCH_2O$—) or difluoromethylenedioxy (—$OCF_2O$—).

The term "halogen" or "halo," as used herein by itself or as part of another group, refers to chlorine, bromine, fluorine or iodine.

The term "monoalkylamine" or "monoalkylamino," as used herein by itself or as part of another group, refers to the group $NH_2$ wherein one hydrogen has been replaced by an alkyl group, as defined above.

The term "dialkylamine" or "dialkylamino," as used herein by itself or as part of another group refers to the group, $NH_2$ wherein both hydrogens have been replaced by alkyl groups, as defined above.

The term "hydroxyalkyl," as used herein as used herein by itself or as part of another group, refers to any of the above alkyl groups wherein one or more hydrogens thereof are substituted by one or more hydroxyl moieties.

The term "acylamino," as used herein refers to a moiety of the formula $NR^aC(O)R^b$, wherein $R^a$ and $R^b$ are independently hydrogen or alkyl groups is defined above.

The term "haloalkyl," as used herein as used herein by itself or as part of another group, refers to any of the above alkyl groups wherein one or more hydrogens thereof are substituted by one or more halo moieties. Typical examples include fluoromethyl, trifluoromethyl, trichloroethyl, and trifluoroethyl.

The term "haloalkenyl," as used herein as used herein by itself or as part of another group, refers to any of the above alkenyl groups wherein one or more hydrogens thereof are substituted by one or more halo moieties. Typical examples include fluoroethenyl, difluoroethenyl, and trichloroethenyl.

The term "haloalkynyl," as used herein as used herein by itself or as part of another group, refers to any of the above alkynyl groups wherein one or more hydrogens thereof are substituted by one or more halo moieties. Typical examples include fluoroethynyl, trifluoroethynyl, and trichloroethynyl.

The term "carboxyalkyl," as used herein as used herein by itself or as part of another group, refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or alkyl, or together with the nitrogen to which they are bound, form a saturated or unsaturated 5-, 6-, or 7-membered ring.

The term "oxy" means an oxygen (O) atom.

The term "thio" means a sulfur (S) atom.

Generally and unless defined otherwise, the phrase "optionally substituted" used herein refers to a group or groups being optionally substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$)alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl)amino, aminocarbonyl, $C_{6-14}$ aryl($C_{1-6}$)alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl($C_{1-6}$)alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, and carboxy($C_{1-6}$)alkylamino.

When the phrase "optionally substituted" is used with reference to an alkyl, alkenyl, or alkynyl group, the phrase "optionally substituted" herein refers to said group or groups being optionally substituted with one or more substituents independently selected from the group consisting of amino, hydroxy, nitro, halogen, cyano, thiol, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$)alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl)amino, $C_{6-14}$ aryl($C_{1-6}$) alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl($C_{1-6}$) alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, and carboxy($C_{1-6}$)alkylamino.

Although detailed definitions have not been provided for every term used above, each term is understood by one of ordinary skill in the art.

Compositions

A composition according to the present invention includes a pharmaceutical composition comprising a compound of Formula I, as defined above, and one or more pharmaceutically acceptable excipients. Preferred compositions of the present invention are pharmaceutical compositions comprising a compound selected from one or more embodiments listed above, and one or more pharmaceutically acceptable excipients. Pharmaceutical compositions that comprise one or more compounds of Formula I may be formulated, as is well known in the prior art, such as by reference to known compilations as Remington's Pharmaceutical Sciences, Mack Publishing Co., Easton, Pa., USA.

In one embodiment of the invention, the composition comprises a compound selected from one or more of the individual embodiments listed above. In another embodiment, the composition comprises a compound selected from the group consisting of any of the specific compounds or subgroups recited above; and pharmaceutically acceptable salts thereof.

In one embodiment, the compositions of the invention comprise from about 0.001 mg to about 1000 mg of a compound of Formula I. In another embodiment, the compositions of the invention comprise from about 0.01 mg to about 10 mg of a compound of Formula I. In another embodiment, the compositions of the invention comprise from about 0.1 mg to about 500 mg of a compound of Formula I. In another embodiment, the composition comprises an amount of a compound of Formula I in an amount sufficient to treat or prevent an inflammatory condition, an inflammatory disease, rheumatoid arthritis, psoriatic arthritis, or cancer, including colon cancer, non small cell lung cancer, and prostate cancer. The amount of compound in each composition may vary depending upon the particular purpose of the pharmaceutical composition. In general, but not always, a composition used to prevent a disease or condition will have a lower amount of compound than a composition used to treat a disease or condition.

The pharmaceutical compositions of the invention can be administered to any animal that can experience the beneficial effects of the compounds of the invention. Foremost among such animals are humans, although the invention is not intended to be so limited. Other suitable animals include canines, felines, dogs, cats, livestock, horses, cattle, sheep, and the like.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions, and cyclodextrin inclusion complexes. Especially preferred alkaline salts are ammonium salts prepared, for example, with Tris, choline hydroxide, Bis-Tris propane, N-methylglucamine, or arginine.

The compounds of this invention may also be administered parenterally as an injectable dosage form in a physiologically acceptable diluent such as sterile liquids or mixtures thereof, including water, saline, aqueous dextrose and other pharmaceutically acceptable sugar solutions, alcohols such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol)-400, a pharmaceutically acceptable oil, fatty acid, fatty acid ester or glyceride, or an acetylated fatty acid glyceride with or without the addition of a pharmaceutically acceptable surfactant, such as a soap or detergent, suspending agent such as pectin, carbomers, methylcellulose, hydroxypropylmethylcellulose, or carboxymethylcellulose, an emulsifying agent or pharmaceutical adjuvants. In all cases, the form should be sterile and should be fluid to the extent that easy syringability exists. It should be stable under the conditions of manufacture and storage and should be preserved against the contaminating action of microorganisms such as bacteria and fungi.

Pharmaceutically acceptable oils which are useful in the formulation herein include those of petroleum, animal, vegetable or synthetic origin, including peanut oil, soybean oil, sesame oil, cottonseed oil, olive oil, sunflower oil, petrolatum, and mineral oil. Fatty acids which may be used include oleic acid, stearic acid, and isostearic acid, while the fatty acid esters useful herein may include ethyl oleate and isopropyl myristate. Suitable soaps include fatty acid alkali metal, ammonium, and triethanolamine salts. Acceptable detergents include cationic detergents, for example, dimethyl dialkyl ammonium halides, alkyl pyridinium halides, and alkylamine acetates and anionic detergents, such as alkyl, aryl, and olefin sulfonates, alkyl, olefin, ether and monoglyceride sulfates, and sulfosuccinates. Useful non-ionic detergents may include fatty amine oxides, fatty acid alkanolamides and polyoxyethylenepolypropylene copolymers. Amphoteric detergents may include alkyl-β-aminopropionates and 2-alkylimidazoline quaternary salts, and mixtures thereof The parenteral compositions of this invention contain, in one embodiment, from about 0.5 to about 25% by weight of the active compounds described herein in solution. The parenteral formulations in the form of sterile injectable solutions or suspensions will also preferably contain from about 0.05% to about 5% suspending agent in an isotonic medium. Buffers and preservatives may be added. A suitable surfactant may also be added. These surfactants may include polyethylene sorbitan fatty acid esters, such as sorbitan monooleate, and the high molecular weight adducts of ethylene oxide with a hydrophobic base, formed by the condensation of propylene oxide with propylene glycol.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

A further form of topical administration is to the eye. The compounds and compositions of the present invention are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 (1976)).

In another embodiment, the present invention is directed to a composition comprising a compound of Formula I and a carrier, wherein said carrier is suitable for an assay. Such carriers may include solid carriers and liquid carriers. A composition suitable for an assay may, but not necessarily, be sterile. Examples of suitable carriers for assays include dimethylsulfoxide, ethanol, dichloromethane, methanol, and the like. In another embodiment, a composition comprises a compound of Formula I and a carrier, wherein the compound is in an amount suitable for inhibiting p38.

Another aspect of the invention is directed to a composition comprising a compound according to Formula I and a protein kinase, such as one or more of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

Uses of the Compounds and Compositions

An additional aspect of the present invention is directed to a method of inducing a conformational change in a protein kinase, wherein the conformational change exposes an allosteric site on said protein kinase. Prior to the invention disclosed herein, it has not been possible to induce and stabilize the conformational change in a protein kinase with a small molecule such that the allosteric site remains exposed and/or stabilized and can be identified and used further, e.g., as in the methods described herein. The conformational change in the protein kinase can be induced by a compound according to Formula I, described above. This conformational change leads to a form of the protein referred to herein as the "open form." In another embodiment, a compound of Formula I is able to stablize the open form of one or more kinases selected from the group consisting of DDR2, EphA1, EphA2, EphA3, EphA5, EphA7, EphA8, c-RAF, Flt1, Flt3, Hck, JNK2α2, JNK3α3, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAPKAP-K2, PDGFR-beta, PKA, PKC-alpha, and Src. In another embodiment, the kines is selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

The open conformation of the protein kinase can be stabilized by a compound of Formula I. In certain embodiments, a compound of Formula I can stabilize the open conformation of the protein kinase sufficiently to enable the crystallization of the protein kinase. In other embodiments, a compound of Formula I can stabilize the open conformation of the protein kinase sufficiently to enable the structure elucidation of the protein kinase using known methods, for example, NMR methods or x-ray diffraction methods.

In one embodiment, the conformational change is induced in the protein kinase by contacting the protein kinase with a compound capable of inducing the conformational change in the p38 protein kinase. A suitable compound includes a compound according to Formula I. The inducer compound can be incubated in a suitable medium with a protein kinase for a period of time to allow the compound to effect the conformational change of the protein kinase. In certain embodiments, the p38 protein kinase and the chemical inducer are incubated for about 1, 5, 10, 20 30, 60, or 100 minutes.

The modulator can contact the protein kinase, such as p38, in a suitable medium.

In one embodiment, a compound of the invention is used to induce a conformational change of the protein kinase in the following medium: 50 µL of 24 mM Tris-HCl buffer, pH 7.5, containing 13 mM $MgCl_2$, 12% Glycerol, 2% DMSO, 2 mM DTT, 2.5 Ci of γ-[$^{33}$P]ATP (1000 Ci/mmol; 1 Ci=37 GBq) (AmershamBiosciense), 10 M ATP (AmershamBiosciense), and 2 M GST-ATF2.

In certain embodiments, a compound that induces and stabilizes the conformational change binds to a protein kinase in a region as described as follows.

The allosteric site on a protein kinase is in one embodiment the pocket near the Asp-Phe-Gly (DFG) motive, of which a large conformational change is generally required for binding of an inhibitor. This region is described for p38 in Pargellis et al., "Inhibition of p38 MAP Kinase by utilizing a novel allosteric binding site," *Nature Structural Biology* 9(4):268-272 (2002), which is hereby incorporated by reference in its entirety. In one embodiment, the allosteric site is the hydrophobic pocket that, in its closed information, is occupied by the DFG motif in a serine-threonine (Ser-Thr) kinase. The hydrophobic pocket can be occupied by a compound of Formula I, resulting in a protein kinase having the open information. In one embodiment, the DFG motif is shifted by about 1 to about 20 Å, compared to its position in the closed conformation. In another embodiment, the DFG motif is shifted from about 5 to about 15 Å, or about 9 to about 10 Å. In one embodiment, the allosteric site is an allosteric site near a DFG motif, or analogous motif, or homologous motif, on a protein selected from the group consisting of DDR2, EphA1, EphA2, EphA3, EphA5, EphA7, EphA8, c-RAF, Flt1, Flt3, Hck, JNK2α2, JNK3α3, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAPKAP-K2, PDGFR-beta, PKA, PKC-alpha, and Src. In another embodiment, the allosteric site is an allosteric site near a DFG motif, or analogous motif, or homologous motif, on a protein selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

Crystallized Kinase in Open Form

In another aspect, the present invention is directed to a protein kinase crystallized in the open form. The crystallized protein kinase in the open form can be used, for example, to design or identify a compound that binds to said protein kinase. The open form of the protein kinase is, in certain embodiments, complexed with a compound that stabilizes the open form of the protein. An example of such a compound is a compound according to Formula I.

In another embodiment, the present invention is directed to a protein kinase crystallized in the open form together with a compound according to Formula I. In another embodiment, the present invention is directed to a protein kinase crystallized in the open form together with a compound according to Formula I, wherein said kinase protein is selected from the group consisting of DDR2, EphA1, EphA2, EphA3, EphA5, EphA7, EphA8, c-RAF, Flt1, Flt3, Hck, JNK2α2, JNK3α3, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAPKAP-K2, PDGFR-beta, PKA, PKC-alpha, and Src. In another embodiment, the present invention is directed to a protein kinase crystallized in the open form together with a compound according to Formula I, wherein said kinase protein is selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

In another embodiment, the protein kinase crystallized in open form with a compound of Formula I is a serine-threonine kinase. In another embodiment, the protein kinase is a mitogen activated protein kinase.

In another aspect, the present invention is directed to a p38 protein kinase crystallized in the open form. The crystallized p38 kinase in the open form can be used, for example, to design or identify a compound that binds to p38. The open form of the protein is preferably complexed with a compound that stabilizes the open form of the protein. An example of such a compound is a compound according to Formula I.

An exemplary crystallized p38 protein kinase in open form according to the present invention includes, but is not limited to, a p38α, p38β, p38γ, p38δ, human forms of p38 kinase, and homology mutants thereof, cocrystallized with a compound of any one of Examples 1-4.

An example of a crystallized protein kinase in open form is human p38 alpha MAP kinase.

In one embodiment, the present invention provides a crystallized p38 protein kinase in the open form. A crystallized p38 protein kinase in the open form has the characteristics as described herein. In one embodiment, the space group of said crystallized p38 protein kinase in the open form is preferably hexagonal. The unit cell dimensions of said space group are defined by a, b, c, α, β, and γ, wherein a is from about 67 Å to about 68 Å, b is from about 76 Å to about 77.00 Å, and c is from about 76.00 Å to about 77.00 Å, preferably they are 67.57, 76.63, and 76.58 respectively, α is about 90 degrees, β is about 90 degrees, and γ is about 90 degrees A crystallized p38 protein kinase in the open form can also be characterized by Matthew's coefficient. In certain embodiments of the crystallized p38 protein kinase in the open form according to the present invention, Matthew's coefficient is from about 2.2 Å$^3$ per Dalton (Da) to about 2.4 Å$^3$ per Da. Preferably, Matthew's coefficient is about 2.3 Å$^3$ per Da. In other embodiments, solvent content is from about 44% to about 50%, preferably from about 46% to about 48%, preferably about 47%.

As used herein, the term "p38 protein kinase" includes naturally and recombinantly produced p38 protein kinase; natural, synthetic, and recombinant biologically active polypeptide fragments of a p38 protein kinase; biologically active polypeptide variants of p38 protein kinase or fragments thereof, including hybrid fusion proteins and dimers; biologically active polypeptide analogs of p38 protein kinase or fragments or variants thereof, including cysteine-substituted analogs. The p38 protein kinase may be generated and/or isolated by any means known in the art. p38 protein kinase and methods of producing p38 protein kinase are disclosed in all of which are fully incorporated by reference herein.

A homologue is a protein that may include one or more amino acid substitutions, deletions, or additions, either from natural mutations of human manipulation. Thus, by way of example, a p38 protein kinase in crystalline, open form may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| Amino Acid Type | Examples of Amino Acids |
|---|---|
| Aromatic | Phenylalanine, Tryptophan, Tyrosine, Histidine |
| Hydrophobic | Leucine, Isoleucine, Valine |
| Polar | Glutamine, Asparagine, Serine, Cysteine |
| Basic | Arginine, Lysine, Histidine |
| Acidic | Aspartic Acid, Glutamic Acid |
| Small | Alanine, Serine, Threonine, Methionine, Glycine |

In one embodiment of the invention, a p38 protein kinase crystallized in the open form comprises, or alternatively consists of, the amino acid sequence of a p38 protein kinase having an amino acid sequence which contains at least one conservative amino acid substitution, but not more than 20 conservative amino acid substitutions. In other embodiments, a p38 protein kinase crystallized in the open form comprises the amino acid sequence of human p38 protein kinase, which contains at least one, but not more than 10, 9, 8, 7, 6, 5, 4, 3, 2 or 1 conservative amino acid substitutions.

By a protein having an amino acid sequence at least, for example, 95% "identical" to a reference amino acid sequence of a p38 protein kinase is intended that the amino acid sequence of the protein is identical to the reference sequence except that the protein sequence may include up to five amino acid alterations per each 100 amino acids of the reference amino acid of the p38 protein kinase. In other words, to obtain a protein having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide or protein is at least 80%, 85%, 90%, 95%, 96%, 97%, 98% or 99% identical to, for instance, the amino acid sequence of a given p38 protein kinase can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In one embodiment, the crystallized protein kinase is complexed with at least one molecule of a compound according to Formula I. In other embodiments, the protein kinase in the open form is complexed with a compound selected from the group consisting of 1-[5-tert-butyl-3-(1,1-dioxo-1$\lambda^6$-[1,2,5] thiadiazepane-5-carbonyl)thiophen-2-yl]-3-[4-(pyridin-4-yloxy)phenyl]urea; 1-[5-tert-butyl-3-(3-oxo-piperazine-1-carbonyl)thiophen-2-yl]-3-[4-(pyridin-4-yloxy)phenyl]urea; 1-[5-tert-butyl-3-(1,1-dioxo-1$\lambda^6$-thiomorpholine-4-carbonyl)thiophen-2-yl]-3-[4-(pyridin-4-yloxy)phenyl]urea; 1-[5-tert-butyl-3-(5-oxo-[1,4]diazepane-1-carbonyl)-thiophen-2-yl]-3-[4-(pyridin-4-yloxy)phenyl]urea; and pharmaceutically acceptable salts thereof. In other embodiments, the protein kinase in the open form is complexed with a compound selected from any of the specific compounds or subgroups of the invention recited above.

Method of Preparing a Crystallized Open Form Kinase

Another aspect of the present invention is directed to a method of preparing a crystallized protein kinase in the open form cocrystallized with a compound of Formula I. The present invention provides methods for preparing a crystallized protein kinase in the open form. Preferably, the method produces a crystallized protein kinase in the open form, wherein said protein kinase diffracts X-rays with sufficiently high resolution to allow determination of the three-dimensional structure of said protein kinase, including atomic coordinates. The three-dimensional structure is useful in a number of methods of the present invention, as described herein. In one embodiment, the protein kinase is selected from the group consisting of DDR2, EphA1, EphA2, EphA3, EphA5, EphA7, EphA8, c-RAF, Flt1, Flt3, Hck, JNK2α2, JNK3α$^3$, JNK3, KDR, Lck, Lyn, MINK, MKK6, Mnk2, MuSK, p38α, p38β, p38γ, p38δ, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAPKAP-K2, PDGFR-beta, PKA, PKC-alpha, and Src. In another embodiment, the protein kinase is selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src.

In one embodiment, the present invention is directed to a method of preparing a crystallized p38 protein kinase in the open form cocrystallized with a compound of Formula I. The present invention provides methods for preparing a crystallized p38 protein kinase in the open form cocrystallized with a compound of Formula I. Preferably, the method produces a crystallized p38 protein kinase in the open form, wherein said p38 protein kinase diffracts X-rays with sufficiently high resolution to allow determination of the three-dimensional structure of said p38 protein kinase, including atomic coordinates. The three-dimensional structure is useful in a number of methods of the present invention, as described herein. Specifically provided is a method for crystallizing a recombinant, non-glycosylated human p38α protein kinase complexed with a compound according to Formula I.

Said protein kinase can be obtained from suitable sources, such as eukaryotic cells or tissues. In general, a protein comprising a p38 protein kinase or a portion thereof is isolated in soluble form in sufficient purity and concentrated for crystallization. The polypeptide is optionally assayed for lack of aggregation (which may interfere with crystallization). The purified polypeptide is preferably crystallized under varying conditions of at least one of the following factors: pH, buffering agent, buffer concentration, salt, polymer, polymer concentration, other precipitating agents, and concentration of p38 protein kinase or portion thereof. See, e.g., Blundell et al., Protein Crystallography, Academic Press, London (1976); McPherson, The Preparation and Analysis of Protein Crystals, Wiley Interscience, N.Y. (1982). The crystallized p38 protein kinase is optionally tested for kinase activity. Differently sized and shaped crystals can further be tested for suitability for X-ray diffraction.

In certain embodiments, the pH of the crystallization solution is from about 6-8, preferably from about 6.5-8. In another embodiment, the pH of the solution is about 7.5.

The crystallization solution can optionally contain a buffering agent. Buffering agents are well-known in the art. Exemplary buffering agents include phosphate, cacodylate, acetates, imidazole, Tris HCl, and sodium HEPES.

In certain embodiments, the buffer concentration is from about 10 millimolar (mM) to about 200 mM.

The salt is an ionic salt, which is well known in the art. Exemplary salts include calcium chloride, sodium citrate, magnesium chloride, ammonium acetate, ammonium sulfate, potassium phosphate, magnesium acetate, zinc acetate, and calcium acetate.

The crystallization solution may contain a polymer. Exemplary polymers that are useful in the present invention include, but not necessarily limited to, polyethylene glycol (PEG), polypropyleneglycol (PPG), and others. The average molecular weight of the polymer is from about 200 to about 100,000. Other suitable values for the average molecular weight of the polymer include from about 200 to about 10,000.

The concentration of the polymer is the concentration of the polymer in the solution suitable for crystallization. In certain embodiments, the concentration of the polymer is from about 1% to about 50%. In other embodiments, the concentration of the polymer is about 1%, 5%, 10%, 20%, 25%, 30%, or 40%.

The solution suitable for crystallization optionally comprises one or more additional agents selected from the group consisting of potassium tartrate, sodium tartrate, ammonium sulfate, sodium acetate, lithium sulfate, sodium formate, sodium citrate, magnesium formate ($Mg(HCO_2)_2$), sodium phosphate, potassium phosphate; $NH_4PO_4$; and 2-propanol.

Any suitable crystallization method is used for crystallizing the p38 protein kinase, or fragment thereof, in the open form thereof. Suitable methods include, but are not limited to, the hanging-drop, vapor diffusion method, microbatch, sitting drop, and dialysis.

In certain embodiments, the crystals are grown for from about 1 hour to about 24 hour.

According to the present invention, one embodiment of preparing a crystallized p38 protein kinase in the open form uses a process as follows. For crystallization, the protein is dialyzed against 25 mM Tris-HCl, pH 7.5, 100 mM NaCl, 10 mM $MgCl_2$, 10 mM DTT, and 5% glycerol and concentrated to 16 mg/ml using an Amicon stirred ultrafiltration cell with YM-10 membrane. The sample aliquots are flashfrozen in liquid nitrogen and stored at −80° C. Protein saturated with a compound according to Formula I is mixed with reservoir solution (10-20% PEG 4000, 0.1M cacodylic acid, pH 6, and 50 mM n-octyl-β-D-glucoside detergent) at a 3:2 protein: solution volume ratio. Hanging or sitting drops of the mixture are placed over the reservoir solution and crystals were grown by vapor difusion. Other embodiments of the invention include a similar procedure in which ratios of the ingredients are varied by +/−10%. In other embodiments, a protein kinase selected from the group consisting of p38α and p38β.

Crystals grown according to the present invention diffract X-rays to at least 10 Å resolution, such as 0.15-10.0 Å, or any range of value therein, such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5, with 3.5 Å or higher resolution being preferred for determining the crystal structure. However, diffraction patterns with a lower resolution, such as 25-3.5 Å, are also useful.

According to certain embodiments of the invention, during growth, some of the crystals are optionally removed, washed, and assayed for biological activity.

In other embodiments, heavy atom derivatives used for multiple isomorphous replacement can be obtained by either soaking the crystals with a mercurial reagent or placing crystals in a gaseous xenon (Xe) atmosphere during data collection (Schiltz et al., J. Appl. Cryst. 27: 950-960 (1994)). Suitable mercurial reagents include sodium p-chloromercuribenzylsulphonate (PCMBS). The concentration of the mercurial reagent is from about 0.1 mM to about 0.5 mM.

An additional aspect of the present invention is a composition comprising a protein kinase, such as p38 protein kinase, and a compound according to Formula I. In other embodiments, the composition further comprises a medium suitable for crystallization of the kinase, such as a p38 protein kinase, in the open form. The medium suitable for crystallization may include but not be limited to a buffering agent, a pH adjusting agent, a salt, a polymer, a precipitating agent, and mixtures thereof.

Another embodiment of the present invention is directed to a composition comprising a compound according to Formula I, a protein kinase, and a carrier that is suitable for crystallization. For example, in one embodiment, the composition comprises a compound according to Formula I, a protein kinase, and water. The composition may optionally further comprise one or more of the following: a buffering agent, a pH adjusting agent, a salt, a polymer, a precipitating agent, and mixtures thereof.

A suitable composition according to the present invention comprises a compound according to Formula I; a protein kinase selected from the group consisting of p38 MAP kinase, c-RAF, Flt3, JNK, Lck, Lun, Tie2, and TRK; water; and a buffering agent. In another embodiment, the composition comprises a protein kinase selected from the group consisting of c-RAF, Flt3, JNK3a3, JNK3, Lck, Lyn, p38α, p38β, p38γ, p38δ, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src; a compound according to Formula I; and a suitable crystallization medium.

Another suitable composition comprises a compound according to Formula I; a protein kinase selected from the group consisting of p38 MAP kinase, c-RAF, Flt3, JNK, Lck, Lun, Tie2, and TRK; water; Tris-HCl and a buffering agent.

Another suitable composition comprises a compound according to Formula I; a protein kinase selected from the group consisting of p38 MAP kinase, c-RAF, Flt3, JNK, Lck, Lun, Tie2, and TRK; water; glycerol; and a buffering agent.

Another suitable composition comprises a compound selected from the group consisting of 1-[5-tert-butyl-3-(1,1-dioxo-1$\lambda^6$-[1,2,5]thiadiazepane-5-carbonyl)thiophen-2-yl]-3-[4-(pyridin-4-yloxy)phenyl]urea, 1-[5-tert-butyl-3-(3-oxo-piperazine-1-carbonyl)thiophen-2-yl]-3-[4-(pyridin-4-yloxy)phenyl]-urea, 1-[5-tert-butyl-3-(1,1-dioxo-1$\lambda^6$-thiomorpholine-4-carbonyl)thiophen-2-yl]-3-[4-(pyridin-4-yloxy)phenyl]urea, and 1-[5-tert-butyl-3-(5-oxo-[1,4]diazepane-1-carbonyl)thiophen-2-yl]-3-[4-(pyridin-4-yloxy)phenyl]urea; a protein kinase; water; and a buffering agent. Another suitable composition comprises a compound selected from any of the specific embodiments or subgroups described herein; a protein kinase; water; and a buffering agent.

Method of Identifying or Designing a Drug

Another aspect of the present invention is directed to a method of identifying or designing a molecule which binds to or fits into an allosteric site of a protein kinase. By designing or identifying a molecule which binds to or fits into an allosteric site of a protein kinase, one may develop said molecule into an effective treatment or prophylactic for certain protein kinase-mediated disease and conditions. By binding to or fitting into the allosteric site, a molecule inhibits the normal function of the protein kinase. By inhibiting the normal function of the protein kinase, the molecule is effective for preventing or treating the aforementioned conditions. One aspect of the present invention is directed to a method of designing or identifying a molecule, comprising employing a process of designing or identifying said molecule, wherein said molecule binds to or fits into an allosteric site of a protein kinase.

An electrostatic potential map of the allosteric site reveals information about the allosteric site that is useful in the process of identifying or designing a molecule according to the present invention. For example, certain portions of the allosteric site are more electronegative, while other areas are more electropositive. To increase the attractive interaction between the molecule and the allosteric site, one would want to identify or design a compound so that an electronegative portion of the molecule is able to interact with the electropositive portion of the allosteric site, and so that an electropositive portion of the molecule is able to interact with the electronegative portion of the allosteric site. Other representations of the electrostatic potential of the allosteric site can be determined using methods known in the art.

A lipophilic potential map of the allosteric site reveals information about the allosteric site that is useful in the process of identifying or designing a molecule according to the present invention. For example, certain portions of the allosteric site are more lipophilic, while other areas are more hydrophilic. To increase the attractive interaction between the molecule and the allosteric site, one would want to identify or design a compound so that a lipophilic portion of the molecule is able to interact with the lipophilic portion of the allosteric site, and so that a hydrophilic portion of the molecule is able to interact with the hydrophilic portion of the allosteric site. Other representations of the lipophilic potential of the allosteric site can be determined using methods known in the art.

Additional features of the allosteric site provide guidance for identifying or designing a molecule according to the method described herein. Therefore, in certain embodiments, it is advantageous to design or identify a molecule wherein said molecule contains at least one aromatic or heteroaryl moiety, for example an thiophene moiety, which interacts with the allosteric site.

An additional aspect of the present invention is identifying or designing a molecule which binds to or fits into an allosteric site, wherein the molecule forms one or more interactions with one or more amino acids of the allosteric site.

In another embodiment, the molecule identified or designed according to the present invention has a predicted affinity of 20 micromolar ($\mu$M) or lower. In other embodiments, the molecule has a predicted affinity of 1 $\mu$M or lower. In other preferred embodiments, the molecule has a predicted affinity of less than 1 $\mu$M, 100 $\mu$M, 10 $\mu$M, or 1 $\lambda$M.

In another embodiment, the molecule identified or designed according to the present invention has a calculated free energy of binding of about −6 to about −16 kcal/mol. In other embodiments, the molecule has a calculated free energy of binding of about −10 to about −14 kcal/mol. In other embodiments, the molecule has a calculated free energy of binding of about −8 to about −12 kcal/mol. Such calculations are with the skill of the ordinary artisan. See, for example, Aqvist, et al., *Accounts Chemical Research* 35(6):358-365 (2002) and references cited therein, which is hereby incorporated by reference.

In another embodiment, the predicted binding energy of a compound designed or identified according to the present invention is from about −10 kcal/mol to about −15 kcal/mol. Other suitable ranges include from about −10 kcal/mol to about −30 kcal/mol, or about −35 kcal/mol. In one embodiment, the predicted binding energy of a molecule or fragment thereof is calculated according to the process described in U.S. Pat. No. 6,735,530 B1, which is hereby incorporated by reference in its entirety.

In another embodiment, the molecule identified or designed according to the present invention has an affinity of 20 micromolar ($\mu$M) or lower. In other embodiments, the molecule has an affinity of 1 $\mu$M or lower. In other preferred embodiments, the molecule has an affinity of less than 100 nM, 10 nM, or 1 nM. Such measurements are within the skill of the artisan. Suitable assays are described herein. In one embodiment, the molecule has an any one of the affinity values listed above as determined in any one of the assays described herein.

Further Uses of the Compounds and Compositions

A further aspect of the present invention is directed to a method of using a compound of Formula I.

A compound according to Formula I is useful for the treatment or prevention of a protein kinase-mediated condition. In one embodiment, the present invention is directed to a method treating, preventing, or ameliorating a protein kinase-mediated condition comprising administering to a subject in need of such treatment an effective amount of a compound according to Formula I. In one embodiment of the invention, the method uses a compound selected from one or more of the individual embodiments listed above. In another embodiment, the protein kinase-mediated condition is a condition mediated by one or more of the kinases selected from the group consisting of DDR2, EphA1, EphA2, EphA3, EphA5, EphA7, EphA8, c-RAF, Flt1, Flt3, Hck, JNK2$\alpha$2, JNK3$\alpha$3, JNK3, KDR, Lck, Lyn, MINK, MKK6, Mnk2, MuSK, p38$\alpha$, p38$\beta$, p38$\gamma$, p38$\delta$, p70S6K, Pyk2, Ret, ROCKI, TAK1, Tie2, TrkA, TrkB, Abl1, Akt1, CK2-alpha 1, c-MET, EGFR, EphB4, ERK2, FGFR1, FGFR2, GSK3-beta, IGF1R, IRAK4, Lck, Lyn A, MAPKAP-K2, PDGFR-beta, PKA, PKC-alpha, and Src. In another embodiment, the protein kinase is selected from the group consisting of c-RAF, Flt3, JNK3$\alpha$3, JNK3, Lck, Lyn, p38$\alpha$, p38$\beta$, p38$\gamma$, p38$\delta$, Tie2, TrkB, Abl1, Akt1, CK2-alpha 1, c-MET, EGFR, EphB4, ERK2, FGFR1, GSK3-beta, IGF1R, IRAK4, Lck, Lyn A, MAPKAP-K2, PDGFR-beta, PKA, PKC-alpha, and Src. In another embodiment, the protein kinase-mediated condition is a condition mediated by one or more of the kinases selected from the group consisting of c-RAF, Flt3, JNK3a3, JNK3, Lck, Lyn, p38α, p38β, p38γ, p38δ, Tie2, and TrkB.

In other embodiments, a compound according to Formula I is useful for the treatment or prevention of a kinase-mediated condition. In one embodiment, the present invention is directed to a method treating, preventing, or ameliorating a kinase-mediated condition comprising administering to a subject in need of such treatment an effective amount of a compound according to Formula I. In one embodiment of the invention, the method uses a compound selected from one or more of the individual embodiments listed above.

In one embodiment, the condition or disease is mediated by p38α.

Another embodiment of the present invention is directed to the treatment or prevention of an inflammatory condition. In one embodiment, the present invention is directed to a method treating, preventing, or ameliorating an inflammatory condition or disease comprising administering to a subject in need of such treatment an effective amount of a compound according to Formula I. In one embodiment of the invention, the method uses a compound selected from one or more of the individual embodiments listed above.

The subject of the method disclosed herein is preferably an animal, including, but not limited, a cow, horse, sheep, pig, chicken, turkey, quail, cat, dog, mouse, rat, rabbit, and guinea pig, and is more preferably a mammal, and most preferably a human.

The term "kinase-mediated condition", as used herein means any disease or other deleterious condition in which a protein kinase is known to play a role. This includes, but is not necessarily limited to, conditions known to be caused by interleukins or TNFs, in particular TNF-α, overproduction. Such conditions include, without limitation, inflammatory diseases, autoimmune diseases, chronic obstructive pulmonary disorder, destructive bone disorders, proliferative disorders, cancer (such as colon cancer, non small cell lung cancer and prostate cancer), infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to acute pancreatitis, chronic pancreatitis, asthma, allergies, and adult respiratory distress syndrome.

The compounds of the invention can be used to prevent or treat diseases involving growth factor dependent angiogenesis such as cancer, macular degeneration and arthritis. Such growth factor angiogenesis may be mediated by angiopoietin 1, vascular endothelial growth factor (VEGF), Fibroblast Growth Factor (FGF), Epithelial growth factor (EGF), and Platelet Derived Growth Factor (PDGF).

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Angiogenic disorders which may be treated or prevented include solid tumors, ocular neovasculization, infantile haemangiomas.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), and CMV retinitis.

Neurodegenerative diseases which may be treated or prevented by the compounds of this invention include, but are not limited to, Alzheimer's disease, Parkinson's disease, and cerebral ischemias or neurodegenerative disease caused by traumatic injury.

A compound and composition of the present invention can be used for the treatment and/or prevention of allergies. In one embodiment, the compound or composition is used to treat or prevent inflammatory symptoms of an allergic reaction. In another embodiment, the compound or composition is used to treat or prevent a respiratory inflammatory response evoked by an allergen.

In another embodiment, a compound or composition of the present invention is used to treat cancer, such as colon cancer, non small cell lung cancer and prostate cancer. In one embodiment, the compound or composition is used to treat a cancer that is associated with chronic inflammation, including but not limited to colorectal cancer, colon cancer, esophageal cancer, mesothelioma, ovarian cancer, and gastric cancer. In another embodiment, the compound or composition is used to treat cancer by blocking tumorigenesis. In another embodiment, the compound or composition is used to treat cancer by inhibiting metastasis. In another embodiment, the compound or composition is used to treat cancer by inducing apoptosis.

A "p38-mediated condition" also includes ischemia/reperfusion in stroke, heart attacks, myocardial ischemia, organ hypoxia, vascular hyperplasia, cardiac hypertrophy, and thrombin-induced platelet aggregation.

A compound of Formula I may further be administered to a subject to inhibit or prevent a healthy subject from developing an inflammatory condition or a p38-mediated condition. A subject, who does not have an inflammatory or p38-mediated condition but may develop one, may be administered a compound according to Formula I to prevent or inhibit the condition. In other words, a compound of Formula I may be used as a prophylactic agent that prevents or inhibits the development of an inflammatory or p38-mediated condition or disease. According to the method, a compound according to Formula I is administered at an dose effective to prevent significant onset of the inflammatory or p38-mediated condition or disease. The presence of the compound of Formula I in or on the subject's body prevents or inhibits the development of the inflammatory or p38-mediated condition or disease.

The compounds of the present invention may be administered in an effective amount within the dosage range of about 0.01 mg/kg to about 300 mg/kg, preferably between 0.1 mg/kg to 100 mg/kg body weight, more preferably from 0.1 mg/kg to 10 mg/kg body weight. Compounds of the present invention may be administered in a single daily dose, or the total daily dosage may be administered in divided doses of, e.g., two, three or four times daily. Those of skill in the treatment of inflammatory conditions and p38-mediated conditions could determine the effective daily amount from the test results presented here. The exact dosage and frequency of administration depends on the particular compound of Formula I used, the particular condition being treated, the severity of the condition being treated, and the age, weight, and general physical condition of the particular patient, as well as other medication the individual may be taking, as is well known to those skilled in the art. The dosages may be varied depending upon the requirements of the patient, the severity of the condition being treated, and the compound being employed. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

A therapeutically effective amount is understood to mean the amount of a compound that, when administered to a mammal for treating a disease, is sufficient to effect such treatment for the disease. The therapeutically effective amount will vary depending on the compound, the disease and its severity and the age, weight, etc., of the mammal to be treated.

Furthermore, the dosages may vary according to the particular usage. For example, a higher amount of a compound of Formula I may be used when treating a subject having a well-developed inflammatory condition, compared to the amount used to prevent a subject from developing the inflammatory condition.

In all cases of administration, it is understood that the compound of Formula I can be administered as a pharmaceutical composition comprising said compound and a pharmaceutically acceptable excipient, as described herein. Alternatively, the compound of Formula I may be administered as a pure material if appropriate.

In an additional aspect of the present invention, a compound of Formula I may be used alone or in combination with one or more additional anti-inflammatory agents. When a compound of the present invention is used along with one or more additional anti-inflammatory agents, the compound of the present invention may be formulated with the other anti-inflammatory agent or agents so that a pharmaceutical composition comprising a compound of Formula I and one or more additional anti-inflammatory agents is administered to an animal. Alternatively, the compound of Formula I can be administered as a separate pharmaceutical composition from the composition comprising the one or more additional anti-inflammatory agents.

The compounds of the present invention are also useful in drug discovery assays. The compounds of Formula I may be used in assays to determine the efficacy and/or potency of other compounds as anti-inflammatory agents or as inhibitors of a protein kinase, such as a p38 kinase. These assays include in vivo and in vitro assays. The compounds of the present invention can be used as controls or can be used as lead compounds to discover new, useful anti-inflammatory compounds or new, useful inhibitors of a kinase, such as a p38 kinase. Additionally, a compound of Formula I may be used to form a crystallized complex with a protein kinase, such as a p38 protein.

The compounds may also be used in inhibiting a protein kinase in vitro or in vivo. The amount of the compound of Formula I used to inhibit a protein kinase may not necessarily be the same when used in vivo compared to in vitro. Factors such as pharmacokinetics and pharmacodynamics of the particular compound may require that a larger or smaller amount of the compound of Formula I be used when inhibiting a protein kinase in vivo. Accordingly, an additional aspect of the present invention is a method of inhibiting a protein kinase, comprising contacting a protein kinase with a compound according to Formula I. In one embodiment of this aspect of the present invention, the method comprises contacting a cell with a compound of Formula I, wherein said cell has a protein kinase. In another embodiment of the present invention, the method comprises administering a compound of Formula I to a subject in an amount sufficient to inhibit a protein kinase, wherein said subject has or expresses a protein kinase. In one embodiment, a compound of the invention is used to inhibit a protein kinase in the following medium: 50 µL of 24 mM Tris-HCl buffer, pH 7.5, containing 13 mM $MgCl_2$, 12% Glycerol, 2% DMSO, 2 mM DTT, 2.5 Ci of $\gamma$-[$^{33}$P]ATP (1000 Ci/mmol; 1 Ci=37 GBq) (AmershamBiosciense), 10 M ATP (AmershamBiosciense), and 2 M GST-ATF2.

In another embodiment of the present invention, a compound of Formula I can be used for preparing a pharmaceutical composition to be used for inhibiting or modulating a protein kinase, for example p38, for treating or preventing an inflammatory condition or disease, or for treating or preventing a protein kinase-mediated condition.

In another embodiment, any one of the methods described herein uses a compound selected from any of the specific compounds or subgroups of the invention recited above, and pharmaceutically acceptable salts thereof.

The biological activity of a compound according to Formula I can be determined by testing said compound using methods known in the art. For example, one can evaluate the ability of a compound to prevent, treat, or inhibit an inflammatory condition by one or more known assays.

In one embodiment, one can evaluate the ability of a compound to inhibit or modulate the activity of a p38 kinase using one or more known assays. One known assay is to test for the inhibition of the p38-catalyzed phosphorylation of EGF receptor peptide by a test compound. EGF receptor peptide is described in published U.S. Patent Application Pub. No. 2003/0149037 (Salituro et al.) and is a phosphoryl acceptor in a p38-catalyzed kinase reaction. The inhibitory activity of the test compound can be determined by comparing the extent of phosphorylation of the EGF receptor peptide in the presence of test compound and in the absence of test compound.

A second assay for testing the p38-inhibitory activity of a compound is a test for inhibition of ATPase activity. This assay determines the ability of a compound to inhibit the ATPase activity of activated p38. The product of p38 ATPase activity, ADP, is quantified by HPLC analysis.

A third assay is another that tests a compound's ability to inhibit p38's kinase activity. This assay, as described in detail in the examples section below, measures the incorporation of $^{33}$P from $\gamma$-[$^{33}$P]ATP into the GST-ATF-2 substrate, amino acids 19-96 (Upstate, N.Y. USA). This incorporation is catalyzed by p38. In the presence of an inhibitory compound, the p38-catalyzed the incorporation of $^{33}$P from $\gamma$-[$^{33}$P]ATP into the GST-ATF-2 substrate is lower.

Another assay which can be used to test a compounds ability to inhibit p38 is one which measures the activation kinetics of p38 by MKK6. The activation of p38 by upstream kinase MKK6 is characterized using, e.g., ELISA. A test compound is preincubated with p38 kinase.

An assay which tests a compound's ability to inhibit TNFα secretion caused by lipopolysaccharide (LPS) can also be used. Such assays are known to one of skill in the art, and an example is described in detail below.

It is further understood that the p38 MAP kinase family of proteins includes at least four different isoforms: α, β, γ, and δ. Other names of p38 MAP kinase include, but are not limited to, cytokine suppressive anti-inflammatory drug-binding protein (CSBP), CSBP kinase, and stress activated protein kinase (SAPK). The sequences of p38 MAP kinases have been disclosed in the following U.S. Pat. Nos. 5,783,664; 5,777,097; 5,955,366; 6,033,873; 5,869,043; 6,444,455 B1; 5,948,885; and 6,376,214 B1.

Additional assays used to determine the kinase activity of a compound according to Formula I are listed below in the Examples section.

Methods of Preparation of Compounds

The compounds for use in the present invention can be synthesized according to methods outlined in the following descriptions. The compounds for use in the present invention can be synthesized using procedures known in the art. The following general schemes illustrate synthetic methods used to prepare compounds of the present invention.

The compounds of the present invention can be prepared using at least one of the methods described below. A compound of Formula I, wherein G is C(O) or $CH_2$, can be prepared according to general Method I, shown in the following scheme:

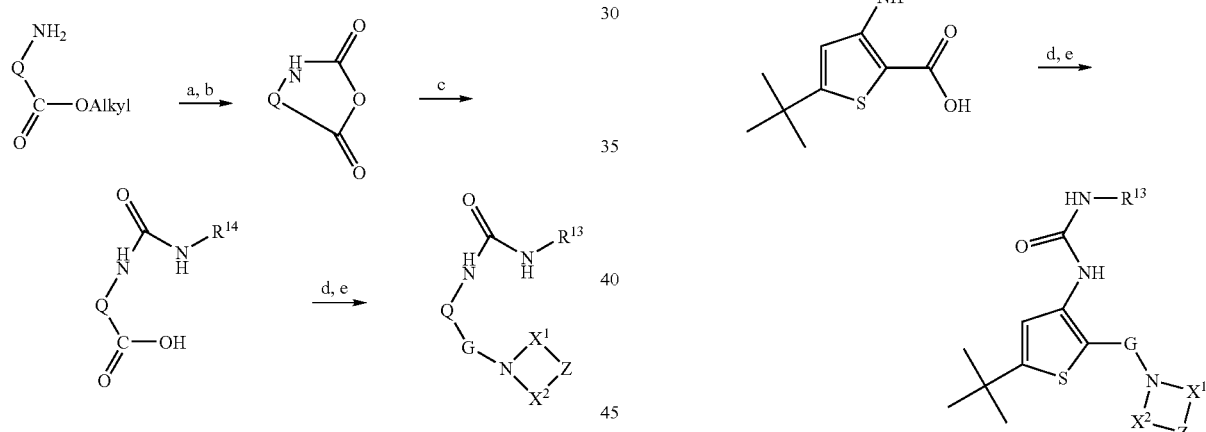

wherein G is $CH_2$ or C(O); Q, $X^1$, $X^2$, and Z are as defined above; and $R^{13}$ is the phenyl group along with $R^1$, $R^2$, and $R^3$, as provided in Formula I. Step a uses a base such as sodium hydroxide or potassium hydroxide to hydrolyze the ester. The resulting acid is then reacted in Step b with phosgene to form the cyclic anhydride, which is then reacted with a suitable amine, $R^{13}$—$NH_2$, to form the carboxylic acid, wherein G is C(O). The carboxylic acid is then reacted with

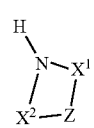

to form a compound according to Formula I, wherein G is C(O). If desired, this compound can be optionally further reacted with a reducing agent, such as $BH_3$-THF, in Step (e) to reduce the C(O) to $CH_2$. In certain, embodiments, a coupling agent may be used in Step d. Suitable coupling agent include an EDCI, 1-hydroxybenzotriazole, and an acid, e.g., HCl.

For example, a compound according to Formula I, wherein G is either C(O) or $CH_2$, can be prepared according to the following scheme:

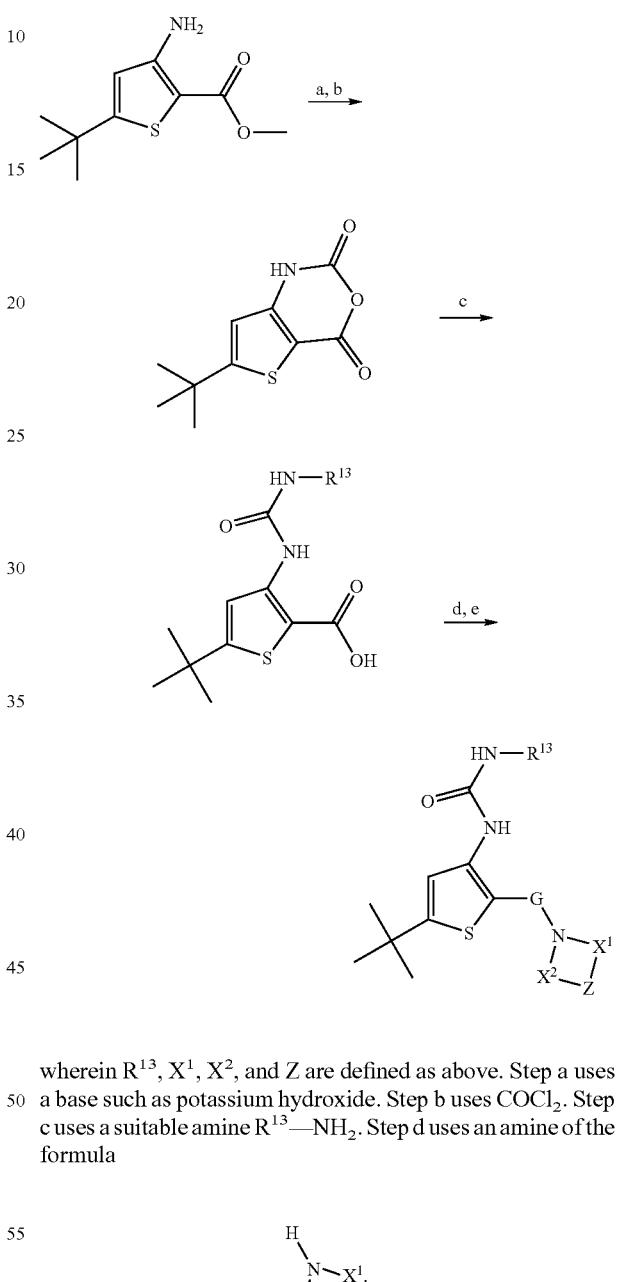

wherein $R^{13}$, $X^1$, $X^2$, and Z are defined as above. Step a uses a base such as potassium hydroxide. Step b uses $COCl_2$. Step c uses a suitable amine $R^{13}$—$NH_2$. Step d uses an amine of the formula $$\begin{array}{c} H \\ \diagdown \\ N \diagup X^1 \\ \diagup \quad \diagup \\ X^2—Z \end{array}$$

Step e uses $BH_3$-THF. An appropriate catalyst or coupling agent, e.g., acid, EDCI, or 1-hydroxybenzotriazole, can be used to effect to formation of the amide in Step d.

By way of another example, a compound according to Formula I, wherein G is either C(O) or $CH_2$, can similarly be prepared according to the following scheme:

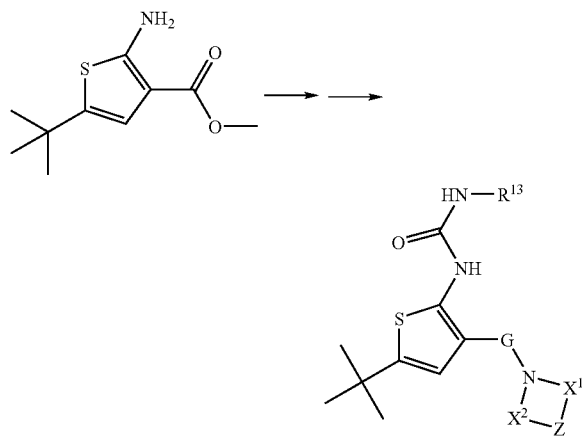

wherein $R^{13}$, $X^1$, $X^2$, and Z are defined as above.

In another method, Method II, a compound according to Formula I wherein G is C(O) and $R^2$ is

can be prepared as shown in the following scheme:

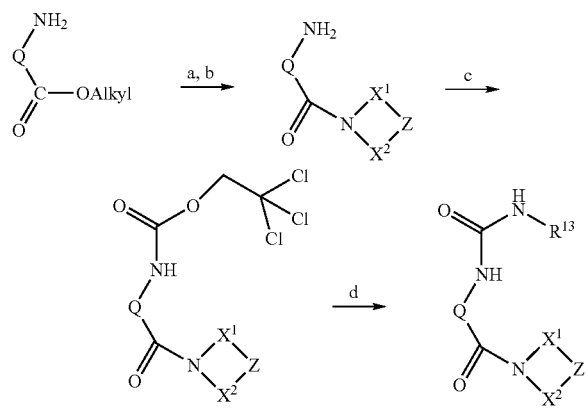

wherein Q, $R^{13}$, $X^1$, and $X^2$ are as defined for Formula I. In Method II, Step a comprises reaching the compound with a base, e.g., NaOH or $K_2CO_3$ to form the acid, which is then reacted with an appropriate amine

to form the amide. The amide is then reacted with 2,2,2-trifluoroethylchloroformate to form the carbamate. The carbamate is then reacted with amine $R^{13}$—$NH_2$ to form a compound of Formula I.

For example, a compound according to Formula I can be prepared according to Method II as follows:

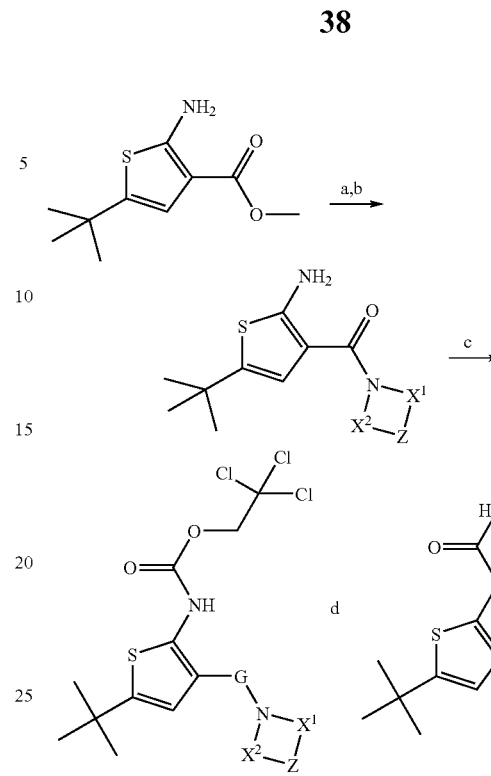

wherein Step a reacts the amino ester with KOH; then the resulting amino acid is reacted with EDCI and HOBT; followed by reacting the amino amide with

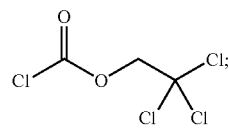

and then forming the urea by reacting $R^{13}$—$NH_2$ with the carbamate.

The corresponding starting amines are either commercially available or can be prepared by methods reported in the literature. Of course, other methods and procedures well known in the art may be used to prepare certain compounds of Formula I.

Of course, other methods and procedures known in the art may be used to prepare certain compounds of Formula I.

The following examples are illustrative, but not limiting, of the method, compounds, and compositions of the present invention. Other suitable modifications and adaptations of the variety of conditions and parameters normally encountered and obvious to those skilled in the art are within the spirit and scope of the invention.

$^1$H-NMR spectra were recorded according to standard procedures. Significant peaks are tabulated in the order: number of protons, multiplicity (s, singlet; d, doublet; t, triplet; q, quartet; m, multiplet; br s, broad singlet) and coupling constant(s) in Hertz.

EXAMPLES

The following description provides procedures that were used to prepare certain compounds according to Formula I and certain intermediates to prepare those compounds.

Example 1

1-(5-tert-Butyl-3-(1,1-dioxo-1λ$^6$-[1,2,5]thiadiazepane-5-carbonyl)thiophen-2-yl)-3-(4-(pyridin-4-yloxy)phenyl)urea

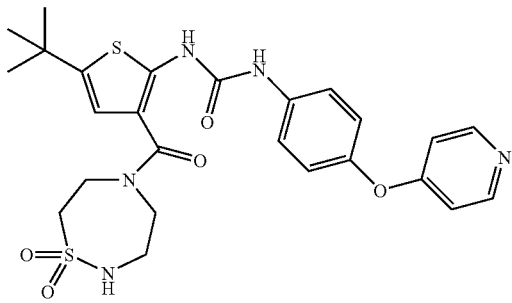

$^1$H NMR (400 MHz, acetone-d$_6$): δ 10.00 (s, 1H), 9.37 (s, 1H), 8.54 (d, J=77.1 Hz, 2H), 7.67 (d, J=8.8 Hz, 2H), 7.11 (d, J=8.8 Hz, 2H), 6.88 (s, 2H), 6.76 (s, 1H), 6.70 (t, J=5.6 Hz, 1H), 4.02 (t, J=5.9 Hz, 2H), 3.98-3.90 (m, 2H), 3.56-3.50 (m, 2H), 3.46 (q, J=5.5 Hz, 2H), 1.36 (s, 9H).

Example 2

1-(5-tert-Butyl-3-(3-oxo-piperazine-1-carbonyl)thiophen-2-yl)-3-(4-(pyridin-4-yloxy)phenyl)urea

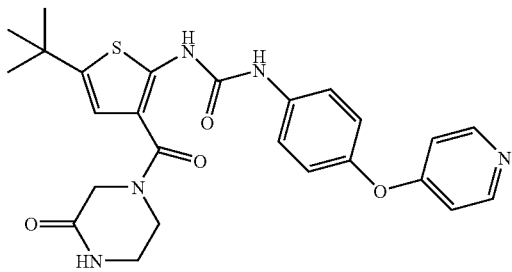

$^1$H NMR (400 MHz, CD$_3$OD/CDCl$_3$): δ 8.32 (d, J=5.3 Hz, 2H), 7.53 (d, J=8.8 Hz, 2H), 7.02 (d, J=9.0 Hz, 2H), 6.86 (d, J=6.2 Hz, 2H), 6.56 (s, 1H), 4.28 (s, 2H), 3.85 (t, J=5.3 Hz, 2H), 3.40 (t, J=5.3 Hz, 2H), 1.35 (d, J=14.1 Hz, 9H).

Example 3

1-[5-tert-Butyl-3-(1,1-dioxo-1λ$^6$-thiomorpholine-4-carbonyl)thiophen-2-yl]-3-[4-(pyridin-4-yloxy)phenyl]urea

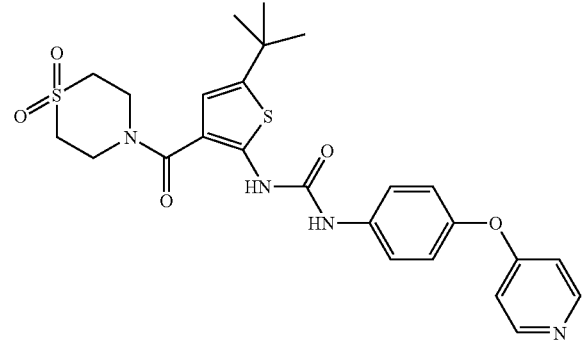

$^1$H NMR (400 MHz, CD$_3$OD): δ 8.35-8.39 (m, 2H), 7.55 (dd, 2H), 7.1 (dd, 2H), 6.9 (dd, 2H), 6.65 (s, 1H), 4.1 (m, 4H), 3.2 (m, 4H), 1.4 (s, 9H).

Example 4

1-(5-tert-Butyl-3-(5-oxo-[1,4]diazepane-1-carbonyl)thiophen-2-yl)-3-(4-(pyridin-4-yloxy)phenyl)urea

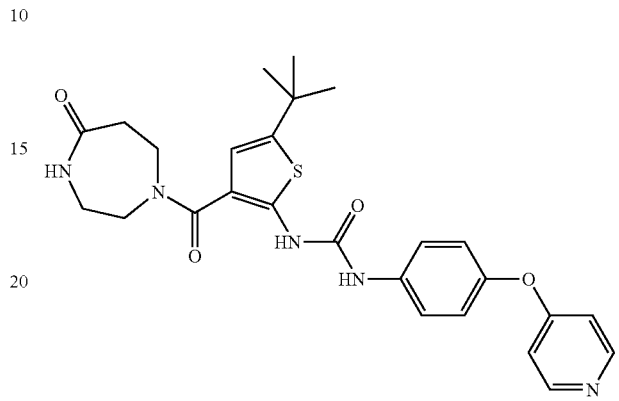

$^1$H NMR (400 MHz, CD$_3$OD/CDCl$_3$): δ 8.35-8.30 (m, 2H), 7.52 (d, J=9.0 Hz, 2H), 7.02 (d, J=9.0 Hz, 2H), 6.89-6.85 (m, 2H), 6.52 (s, 1H), 3.80-3.73 (m, 4H), 3.39-3.34 (m, 2H), 2.76-2.70 (m, 2H), 1.34 (s, 9H).

Example 5

1-(5-tert-Butyl-3-(thiomorpholine-1,1-dioxide-4-carbonyl)thiophen-2-yl)-3-(4-(2-(methylcarbamoyl)pyridin-4-yloxy)phenyl)urea

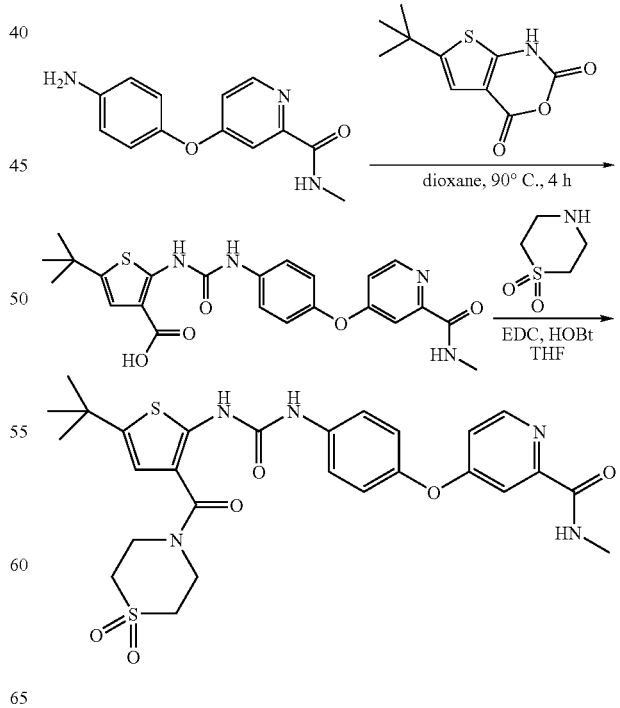

To a solution of 6-tert-butyl-1H-thieno[2,3-d][1,3]oxazine-2,4-dione (3.7 g, 15 mmol) in dioxane (30 mL) was added 4-(4-aminophenoxy)-N-methylpicolinamide (3.4 g, 14 mmol), and the reaction mixture was heated at 90° C. for 4 h. The volatiles were evaporated under reduced pressure to give the crude product which was used in the next step without further purification.

To a solution of 5-tert-butyl-2-(3-(4-(pyridin-4-yloxy)phenyl)ureido)thiophene-3-carboxylic acid (ca 14 mmol) in THF (70 mL) were added thiomorpholine 1,1-dioxide (2.27 g, 16.8 mmol, 1.2 eq), HOBt (2.08 g, 15.4 mmol, 1.1 eq), EDCI (3.22 g, 16.8 mmol, 1.2 eq), and the mixture was stirred at room temperature for 16 h. The volatiles were evaporated under reduced pressure to give the crude product which was extracted with saturated sodium bicarbonate (3×40 mL) and ethyl acetate (150 mL). The organic layer was dried and diluted with ethanol (40 mL). Upon concentration of the solution using rotary evaporator, precipitation of solid occurred. The solid was digested with ethanol (70 mL), filtered, washed with ethanol to give the product which was dried under vacuum at 70° C. for 24 h. (yield=7.2 g, 82%). $^1$H NMR (400 MHz, DMSO-d$_6$) δ 9.89 (s, 1H), 9.63 (s, 1H), 8.73 (m, 1H), 8.47 (d, J=6.8 Hz, 1H), 7.54 (d, J=8.8 Hz, 2H), 7.35 (d, J=2.8 Hz, 1H), 7.13 (d, J=8.8 Hz, 2H), 7.11 (m, 1H0, 6.65 (s, 1H), 3.93 (m, 4H), 3.27 (m, 4H), 2.75 (d, J=5.2 Hz, 3H), 1.30 (s, 9H).

Example 6

1-(5-tert-Butyl-3-(1,2,5-thiadiazepane-1,1-dioxide-5-carbonyl)thiophen-2-yl)-3-(4-(2-(methylcarbamoyl)pyridin-4-yloxy)phenyl)urea

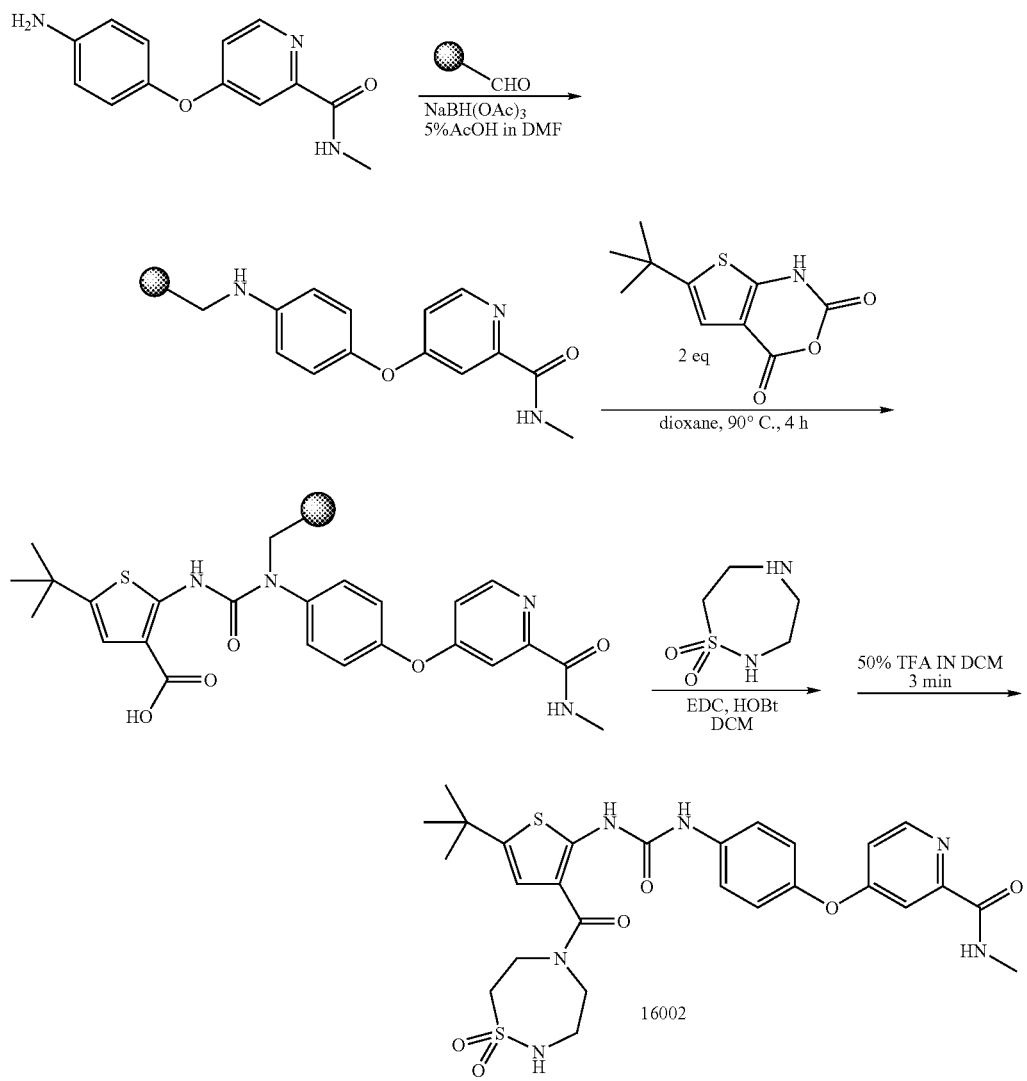

BAL aldehyde resin (0.5 g, 1 mmol/g, 0.5 mmol) was placed into a 20 mL syringe reactor. A solution of 4-(4-aminophenoxy)-N-methylpicolinamide (243 mg, 1.0 mmol) in 5% AcOH in DMF (3 mL) was charged to the syringe, and the syringe was shaken for 2 h. A solution of NaBH(OAc)$_3$ (212 mg, 1.0 mmol) in 5% AcOH in DMF (2 mL) was added to the syringe. After shaking for at room temperature for 2 h, additional solution of NaBH(OAc)$_3$ (212 mg, 1.0 mmol) in 5% AcOH in DMF (2 mL) was added to the syringe and the reaction was shaken overnight. The resin was washed with 5% AcOH in DMF (2×10 mL), DMF (2×10 mL), DCM (2×10 mL), 10% diisopropylethylamine in DCM (2×10 mL), DCM (4×10 mL), and dried in vacuo.

The secondary amine resin (0.25 mmol) was treated with a solution of 6-tert-butyl-1H-thieno[2,3-d][1,3]oxazine-2,4-dione (113 mg, 0.50 mmol) in dioxane (4 mL), and the reaction mixture was heated at 100° C. for 16 h. The resin was washed with THF (2×4 mL), DCM (4×4 mL), and dried under vacuum.

The acid intermediate on resin (0.1 mmol) was treated with EDCI (96 mg, 0.5 mmol), HOBt (68 mg, 0.5 mmol) and secondary amine (75.1 mg, 0.5 mmol) in DCM (2 mL) at room temperature for 3 h, washed with DCM (2×4 mL), MeOH (2×4 mL), and DCM (3×4 mL), and dried under vacuum.

The resin prepared above (0.1 mmol) was treated with 50% TFA/DCM (2 mL) for 3 min in a 5 mL syringe, and the cleavage solution was filtered. The resin was washed with DCM (1 mL), and the combined solution was evaporated by nitrogen blowing under mild heating to give the product which was extracted with ethyl acetate/aqueous NaHCO$_3$. The organic layer was dried, evaporated to give the desired product as a white solid. (yield=44.5 mg). $^1$H NMR: (400 MHz, CD$_3$OD) δ 8.49 (d, J=6.0 Hz, 1H), 7.65 (d, J=2.4 Hz, 1H), 7.58 (d, J=8.8 Hz, 2H), 7.17 (dd, J=6.0, 2.8 Hz, 1H), 7.13 (d, J=8.8 Hz, 2H), 6.69 (d, 1H), 3.90 (m, 2H), 3.87 (t, J=6.0 Hz, 2H), 3.51 (m, 2H), 3.32 (t, J=6.0 Hz, 2H), 2.93 (s, 3H), 1.36 (s, 9H).

Example 7

1-(5-tert-Butyl-3-(5-oxo-1,4-diazepane-1-carbonyl)thiophen-2-yl)-3-(4-(2-(methylcarbamoyl)pyridin-4-yloxy)phenyl)urea

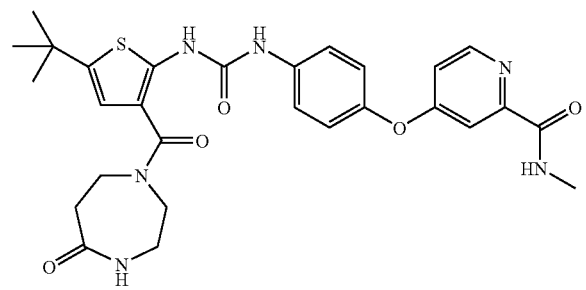

The compound of this example was prepared using a procedure analogous to that used in Example 6, except that 1,4-diazepan-5-one was used instead of 1,1-dioxo-1,2,5-thiadiazepane. $^1$H NMR (400 MHz, CD$_3$OD) δ 8.42 (dd, J=2.0, 0.8 Hz, 1H), 7.54 (d, J=8.8 Hz, 2H), 7.53 (m, 1H), 7.08 (d, J=8.8 Hz, 2H), 7.01 (m, 1H), 6.60 (s, 1H), 3.77 (m, 4H), 3.38 (m, 2H), 2.91 (s, 1H), 2.75 (m, 2H), 1.36 (s, 9H).

Example 8

1-(5-tert-Butyl-3-(2-oxopiperazine-4-carbonyl)thiophen-2-yl)-3-(4-(2-(methylcarbamoyl)pyridin-4-yloxy)phenyl)urea

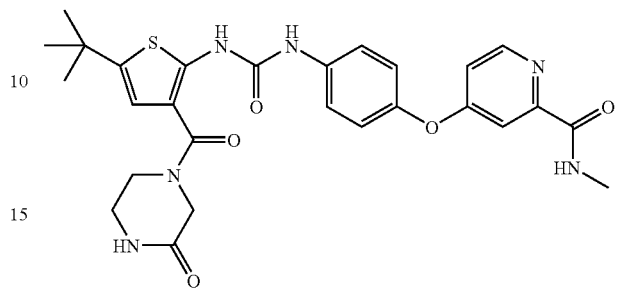

The compound of this example was prepared using a procedure analogous to that used in Example 6, except that piperazin-2-one was used instead of 1,1-dioxo-1,2,5-thiadiazepane. $^1$H NMR: (400 MHz, CD$_3$OD) δ 8.39 (d, J=5.6 Hz, 1H), 7.52 (dd, J=6.8, 2.0 Hz, 2H), 7.50 (s, 1H), 7.03 (dd, J=6.8, 2.0 Hz, 2H), 6.97 (dd, J=6.0, 2.8 Hz, 1H), 6.63 (s, 1H), 4.28 (s, 2H), 3.83 (m, 2H), 3.37 (m, 2H), 2.90 (s, 3H), 1.33 (s, 9H).

Example 9

1-(5-tert-Butyl-2-(thiomorpholine-1,1-dioxide-4-carbonyl)thiophen-3-yl)-3-(4-(2-(methylcarbamoyl)pyridin-4-yloxy)phenyl)urea

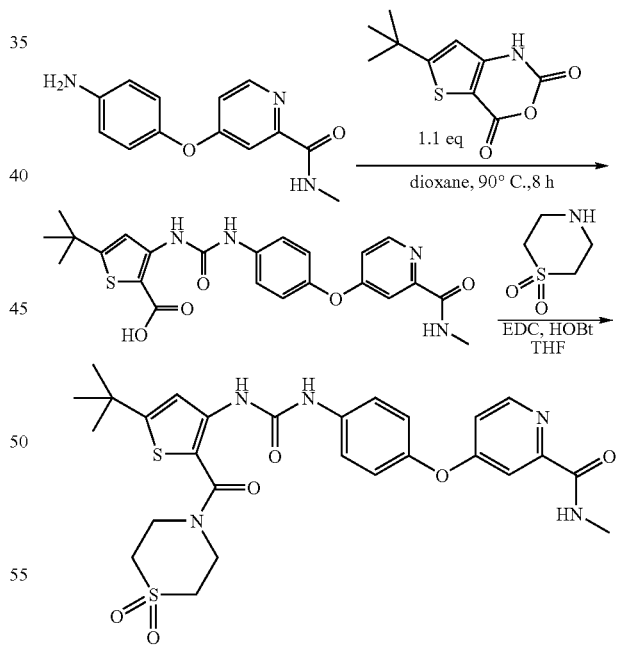

4-(4-aminophenoxy)-N-methylpicolinamide (3.4 g, 14 mmol) was treated with a solution of 6-tert-butyl-1H-thieno[3,2-d][1,3]oxazine-2,4-dione (MW=225.26, 3.7 g, 15 mmol) in dioxane (30 mL), and the reaction mixture was heated at 90° C. for 8 h.

The volatiles were evaporated under reduced pressure to give the crude product. To a solution of 5-tert-butyl-3-(3-(4-(2-(methylcarbamoyl)pyridin-4-yloxy)phenyl)ureido)thiophene-2-carboxylic acid (1.4 mmol) in THF (70 mL)

were added thiomorpholine 1,1-dioxide (2.27 g, 16.8 mmol, 1.2 eq), HOBt (2.08 g, 15.4 mmol, 1.1 eq), EDCI (3.22 g, 16.8 mmol, 1.2 eq), and the mixture was stirred at room temperature for 16 h. The volatiles were evaporated under reduced pressure to give the crude product which was extracted with saturated sodium bicarbonate (3×50 mL) and ethyl acetate (150 mL). The organic layer was dried and concentrated to give the crude product which was dissolved in MeOH (30 mL). The solid precipitated was filtered, washed with methanol (20 mL), and dried to give the desired product (6.0 g, 73%). $^1$H NMR: (400 MHz, DMSO-$d_6$) δ 9.65 (s, 1H), 9.31 (s, 1H), 8.72 (m, 1H), 8.47 (d, J=6.0 Hz, 1H), 7.58 (m, 1H), 7.56 (dd, J=6.8, 2.0 Hz, 2H), 7.34 (d, J=2.4 Hz, 1H), 7.12 (dd, J=6.8, 2.0 Hz, 2H), 7.10 (m, 1H), 4.03 (m, 4H), 3.26 (m, 4H), 2.75 (d, J=4.8 Hz, 3H), 1.33 (s, (H).

Example 10

1-(5-tert-Butyl-3-(thiomorpholine-4-carbonyl)thiophen-2-yl)-3-(4-(pyridin-4-yloxy)phenyl)urea

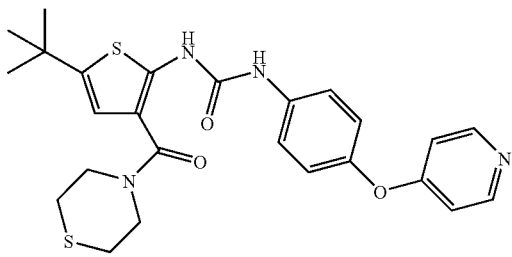

To a vial containing urea acid (60.6 mg, 0.147 mmol, 1 equiv.), EDCI (34.2 mg, 0.178 mmol, 1.2 equiv.) and HOBt (21.2 mg, 0.157 mmol, 1.1 equiv.) in 1 mL THF was added thiomorpholine (0.015 mL, 0.158 mmol, 1.1 equiv.). The vial was capped and the reaction mixture was stirred at r.t. After 21 h the reaction solution was diluted with ethyl acetate and washed with saturated NaHCO$_3$ (×1), water (×1) and brine (×1). The organic layer was dried over Na$_2$SO$_4$, filtered and solvent was removed under vacuum. Purification by preparative TLC using 93:7 dichloromethane:methanol gave 60.8 mg (83%) of the desired product as an off white solid.

$^1$H NMR (400 MHz, CD$_3$OD): δ 8.35 (d, J=5.9 Hz, 2H), 7.52 (d, J=8.8 Hz, 2H), 7.05 (d, J=8.8 Hz, 2H), 6.90 (d, J=6.1 Hz, 2H), 6.56 (s, 1H), 3.89 (t, J=4.6 Hz, 4H), 2.66 (t, J=4.7 Hz, 4H), 1.33 (s, 9H)

Example 11

1-(5-tert-Butyl-3-(morpholine-4-carbonyl)thiophen-2-yl)-3-(4-(pyridin-4-yloxy)phenyl)urea

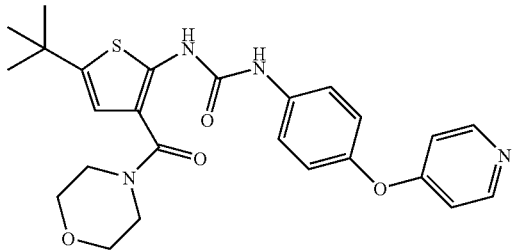

The reaction was performed as above (method 1) to give 86% of the desired product as an light yellow solid. $^1$H NMR (400 MHz, CD$_3$OD): δ 8.35 (dd, J=5.0, 1.5 Hz, 2H), 7.53 (q, J=3.0 Hz, 2H), 7.05 (d, J=9.0 Hz, 2H), 6.90 (dd, J=5.0, 1.5 Hz, 2H), 6.59 (s, 1H), 3.67 (s, 8H), 1.33 (s, 9H)

Example 12

1-(5-tert-Butyl-2-(2-oxopiperazine-4-carbonyl)thiophen-3-yl)-3-(4-(2-(methylcarbamoyl)pyridin-4-yloxy)phenyl)urea

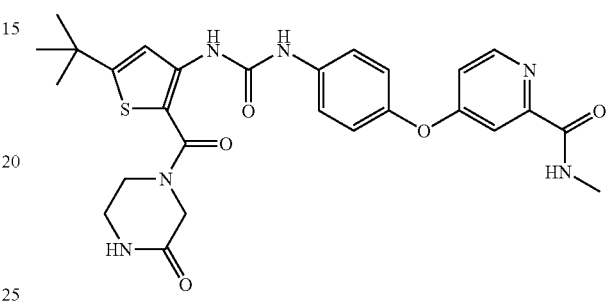

The compound of this example was prepared using a procedure analogous to that used in Example 8, except that 6-tert-butyl-1H-thieno[3,2-d][1,3]oxazine-2,4-dione was used instead of 6-tert-butyl-1H-thieno[2,3-d][1,3]oxazine-2,4-dione. $^1$H NMR: (400 MHz, CD$_3$OD) δ 8.40 (m, 1H), 7.60 (m, 1H), 7.54 (d, J=8.0 Hz, 2H), 7.52 (m, 1H), 7.05 (d, J=8.0 Hz, 2H), 6.99 (m, 1H), 4.33 (s, 2H), 3.94 (t, J=5.2 Hz, 2H), 3.40 (t, J=5.2 Hz, 2H), 2.91 (d, J=1.2 Hz, 3H), 1.38 (s, 9H).

Example 13

1-(5-tert-Butyl-2-(5-oxo-1,4-diazepane-1-carbonyl)thiophen-3-yl)-3-(4-(2-(methylcarbamoyl)pyridin-4-yloxy)phenyl)urea

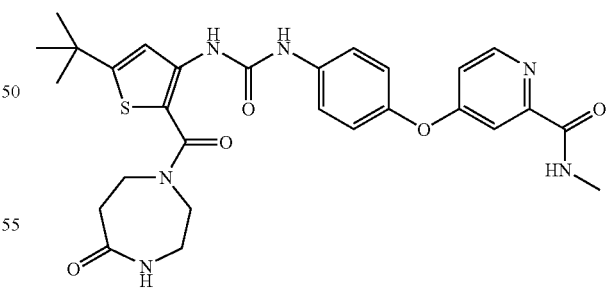

The compound of this example was prepared using a procedure analogous to that used in Example 7, except that 1,4-diazepan-5-one was used instead of 1,1-dioxo-1,2,5-thiadiazepane. $^1$H NMR: (400 MHz, CD$_3$OD) δ 8.40 (m, 1H), 7.57 (s, 1H), 7.52 (d, J=9.2 Hz, 2H), 7.04 (d, J=9.2 Hz, 2H), 6.99 (m, 1H), 3.85 (m, 4H), 3.39 (m, 2H), 2.91 (s, 3H), 2.74 (m, 2H), 1.37 (s, 9H).

Example 14

1-(5-tert-Butyl-2-(1,2,5-thiadiazepane-1,1-dioxide-5-carbonyl)thiophen-3-yl)-3-(4-(2-(methylcarbamoyl)pyridin-4-yloxy)phenyl)urea

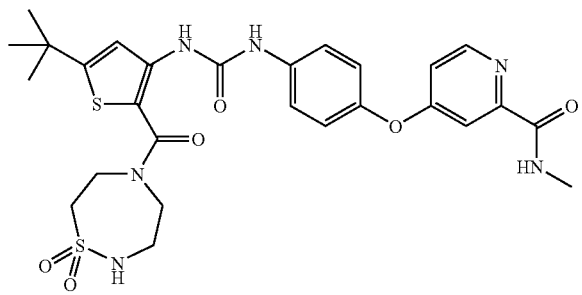

The compound of this example was prepared using a procedure analogous to that used in Example 6, except that 6-tert-Butyl-1H-thieno[3,2-d][1,3]oxazine-2,4-dione was used instead of 6-tert-Butyl-1H-thieno[2,3-d][1,3]oxazine-2,4-dione. $^1$H NMR: (400 MHz, DMSO-$d_6$) δ 9.96 (s, 1H), 9.83 (s, 1H), 8.72 (m, 1H), 8.47 (d, J=6.4 Hz, 1H), 7.74 (s, 1H), 7.59 (d, J=8.4 Hz, 1H), 7.43 (m, 1H), 7.43 (m, 1H), 7.34 (d, J=2.4 Hz, 1H), 7.12 (d, J=8.4 Hz, 1H), 7.10 (m, 1H), 3.92 (m, 2H), 3.87 (m, 2H), 3.46 (m, 2H), 3.26 (m, 2H), 2.75 (d, J=4.4 Hz, 3H), 1.33 (s, 9H).

Example 15

1-(5-tert-Butyl-3-(thiomorpholine-1,1-dioxide-4-carbonyl)thiophen-2-yl)-3-(4-(pyridin-4-ylmethoxy)phenyl)urea

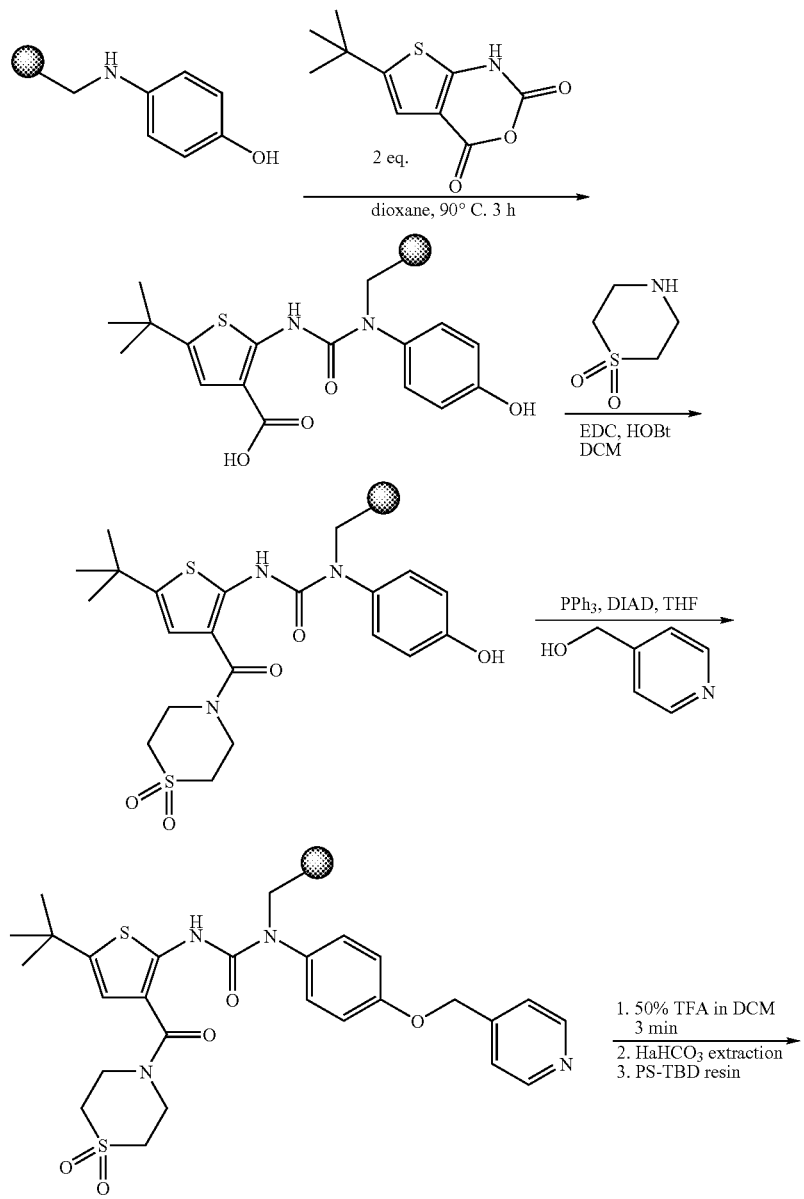

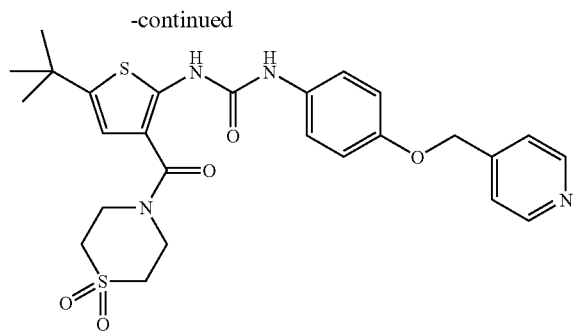

The secondary amine resin (0.25 mmol) was treated with a solution of 6-tert-butyl-1H-thieno[2,3-d][1,3]oxazine-2,4-dione (113 mg, 0.50 mmol) in dioxane (4 mL), and the reaction mixture was heated at 90° C. for 3 h. The resin was washed with THF (2×4 mL), DCM (4×4 mL), and dried under vacuum. The acid intermediate on resin (0.1 mmol) was treated with EDCI (96 mg, 0.5 mmol), HOBt (68 mg, 0.5 mmol) and thiomorpholine 1,1-dioxide (68 mg, 0.5 mmol) in DCM (2 mL) at room temperature for 3 h, washed with DCM (2×3 mL), THF (2×3 mL), DCM (3×3 mL), and dried under vacuum.

To the resin-bound intermediate prepared above were added 4-pyridine methanol (54.5 mg, 0.4 mmol) and triphenyl phosphine (79 mg, 0.3 mmol) in THF (3 mL). After cooling the syringe in dry ice for a few minutes, a solution of diisopropyl azodicarboxylate (DIAD, 71 mg, 0.35 mmol) in THF (1 mL) was added to the syringe, and the syringe was shaken for at room temperature 16 h. The resin was washed with THF (4×4 mL), MeOH (4×4 mL), DCM (4×4 mL), and dried under high vacuum.

The resin prepared above (0.1 mmol) was treated with 50% TFA/DCM (2 mL) for 3 min in a 5 mL syringe, and the cleavage solution was filtered. The resin was washed with DCM (1 mL), and the combined solution was evaporated by nitrogen blowing under mild heating to give the product which was extracted with ethyl acetate/aq NaHCO₃. The organic layer was dried, evaporated to give the crude products (desired compound was a major component plus ca 20% phenol side product which was removed by the following step).

The crude product was stirred with PS-TBS resin (100 mg) in MeOH for 2 h. The reaction was filtered, and the filtrate was concentrated to provide the desired product. (Yield=9.0 mg). $^1$H NMR (400 MHz, CD$_3$OD) δ 8.42 (dd, J=4.8, 1.6 Hz, 2H), 7.41 (m, 2H), 7.26 (d, J=8.8 Hz, 2H), 6.87 (d, J=8.8 Hz, 2H), 6.55 (s, 1H), 5.06 (s, 2H), 4.00 (m, 4H), 3.11 (m, 4H), 1.27 (s, 9H).

Example 16

1-(2-tert-Butyl-4-(thiomorpholine-1,1-dioxide-4-carbonyl)thiazol-5-yl)-3-(4-(pyridin-4-yloxy)phenyl)urea

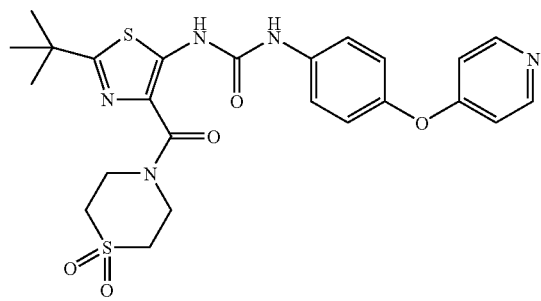

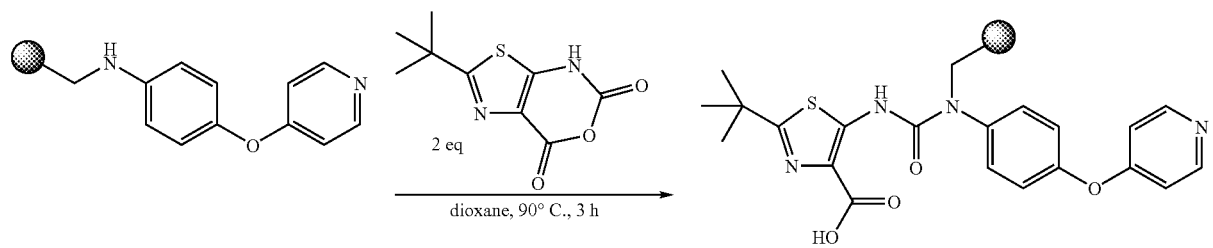

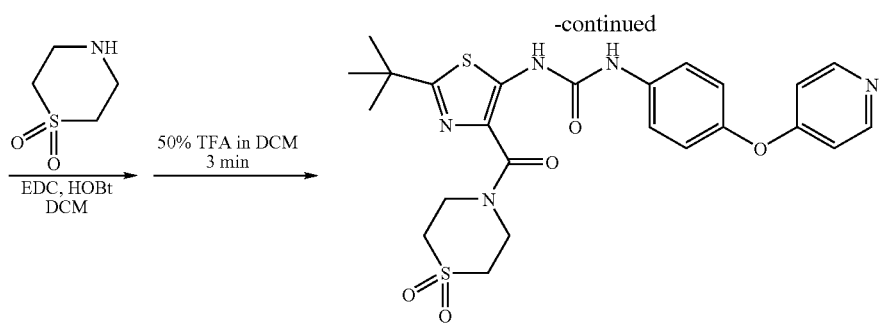

The secondary amine resin (0.1 mmol) was treated with a solution of 2-tert-butyl-4H-thiazolo[5,4-d][1,3]oxazine-5,7-dione (45 mg, 0.20 mmol) in dioxane (2 mL), and the reaction mixture was heated to 90° C. for 3 h. The resin was washed with THF (2×3 mL), DCM (4×3 mL), and dried under vacuum.

The acid intermediate on resin (0.05 mmol) was treated with EDCI (48 mg, 0.25 mmol), HOBt (12, 34 mg, 0.25 mmol) and thiomorpholine 1,1-dioxide (34 mg, 0.25 mmol) in dichloromethane (2 mL) for 3 h at room temperature, and washed with dichloromethane (2×3 mL), THF (2×3 mL), dichloromethane (3×3 mL), and dried under vacuum The resin prepared above (0.05 mmol) was treated with 50% TFA: dichloromethane (2 mL) for 3 min in a 5 mL syringe, and the cleavage solution was filtered. The resin was washed with dichloromethane (1 mL), and the combined solution was evaporated by nitrogen blowing under mild heating to give the product which was extracted with ethyl acetate: aq NaHCO$_3$. The organic layer was dried, evaporated to give a crude product which was purified by preartive SFC to give the desired product as a solid. (Yield=4.4 mg) (400 MHz, CD$_3$OD) δ 8.37 (d, J=6.0 Hz, 2H), 7.58 (d, J=8.8 Hz, 2H), 7.10 (d, J=8.8 Hz, 2H), 6.93 (d, J=6.0 Hz, 2H), 4.74 (bs, 2H), 4.20 (bs, 2H), 3.25 (bs, 4H), 1.40 (s, 9H).

Example 17

1-(5-tert-Butyl-3-(thiomorpholine-1-oxide-4-carbonyl)thiophen-2-yl)-3-(4-(pyridin-4-yloxy)phenyl)urea

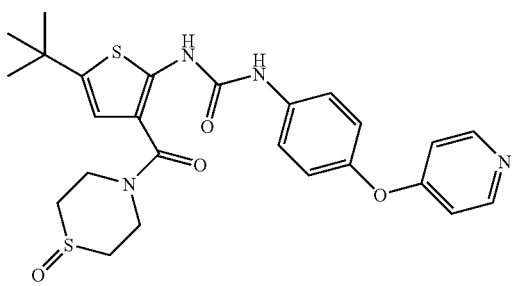

The reaction was performed as above (method 1) using oxothiomorpholine (J. Org. Chem. 1962, 27, 282-284) to give 83% of the desired product as an off white solid. $^1$H NMR (400 MHz, CD$_3$OD): δ 8.35 (dd, J=5.0, 1.4 Hz, 2H), 7.53 (d, J=9.0 Hz, 2H), 7.05 (d, J=9.0 Hz, 2H), 6.90 (dd, J=5.0, 1.5 Hz, 2H), 6.63 (s, 1H), 4.21 (d, J=14.4 Hz, 2H), 3.98 (t, J=12.1 Hz, 2H), 3.02 (ddd, J=13.9, 11.1, 3.1 Hz, 2H), 2.91 (d, J=13.9 Hz, 2H), 1.34 (s, 9H)

Example 18

1-(5-tert-Butyl-2-(thiomorpholine-1,1-dioxide-4-carbonyl)thiophen-3-yl)-3-(4-(pyridin-4-yloxy)phenyl)urea

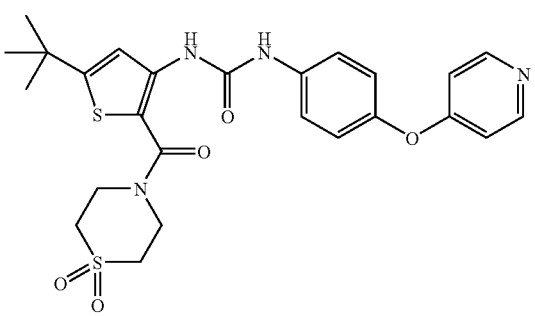

The compound of this example was prepared using a procedure analogous to that used in Example 9, except that 4-(pyridin-4-yloxy)phenylamine was used instead of 4-(4-aminophenoxy)-N-methylpicolinamide. $^1$H NMR: (400 MHz, CD$_3$OD) δ 8.36 (d, J=6.0 Hz, 2H), 7.55 (d, J=8.8 Hz, 2H), 7.45 (s, 1H), 7.06 (d, J=8.8 Hz, 2H), 6.91 (d, J=6.0 Hz, 2H), 4.18 (m, 4H), 3.23 (m, 4H), 1.38 (s, 9H).

Example 19

1-(5-tert-Butyl-2-(2-oxopiperazine-4-carbonyl)thiophen-3-yl)-3-(4-(pyridin-4-yloxy)phenyl)urea

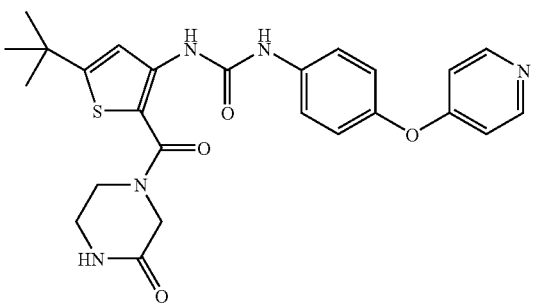

The compound of this example was prepared using a procedure analogous to that used in Example 12, except that 4-(pyridin-4-yloxy)phenylamine was used instead of 4-(4-aminophenoxy)-N-methylpicolinamide. $^1$H NMR: (400

MHz, CD₃OD) δ 8.35 (d, J=6.0 Hz, 2H), 7.61 (m, 1H), 7.55 (d, J=8.8 Hz, 2H), 7.06 (d, J=8.8 Hz, 2H), 6.91 (d, J=6.0 Hz, 2H), 4.33 (s, 2H), 3.95 (t, J=5.2 Hz, 2H), 3.41 (t, J=5.2 Hz, 2H), 1.39 (s, 9H).

Example 20

1-(5-tert-Butyl-2-(1,2,5-thiadiazepane-1,1-dioxide-5-carbonyl)thiophen-3-yl)-3-(4-(pyridin-4-yloxy)phenyl)urea

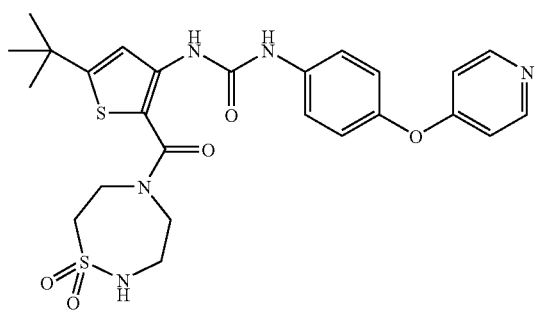

The compound of this example was prepared using a procedure analogous to that used in Example 6, except that 4-(pyridin-4-yloxy)phenylamine was used instead of 4-(4-aminophenoxy)-N-methylpicolinamide. ¹H NMR: (400 MHz, CD₃OD) δ 8.35 (d, J=6.0 Hz, 2H), 7.55 (d, J=8.8 Hz, 2H), 7.53 (s, 1H), 7.06 (d, J=8.8 Hz, 2H), 6.91 (d, J=6.0 Hz, 2H), 4.02 (m, 2H), 3.99 (m, 2H), 3.51 (m, 2H), 3.35 (m, 2H), 1.39 (s, 9H).

Example 21

1-(5-tert-Butyl-2-(5-oxo-1,4-diazepane-1-carbonyl)thiophen-3-yl)-3-(4-(pyridin-4-yloxy)phenyl)urea

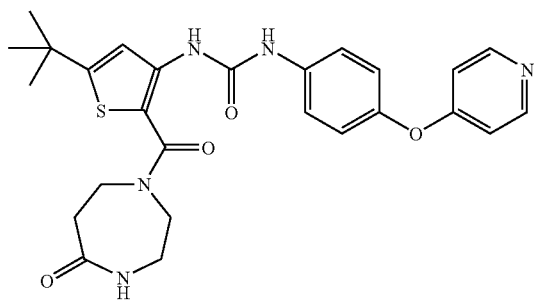

The compound of this example was prepared using a procedure analogous to that used in Example 7, except that nylamine was used instead of 4-(4-aminophenoxy)-N-methylpicolinamide. ¹H NMR: (400 MHz, CD₃OD) δ 8.36 (d, J=7.2 Hz, 2H), 7.57 (s, 1H), 7.54 (d, J=8.8 Hz, 2H), 7.07 (d, J=8.8 Hz, 2H), 6.92 (d, J=7.2 Hz, 2H), 3.88 (m, 4H), 3.39 (m, 2H), 2.75 (m, 2H), 1.39 (s, 9H).

Example 22

1-(5-tert-Butyl-3-(thiomorpholine-1,1-dioxide-4-carbonyl)thiophen-2-yl)-3-(4-(3,5-dichloropyridin-4-yloxy)phenyl)urea

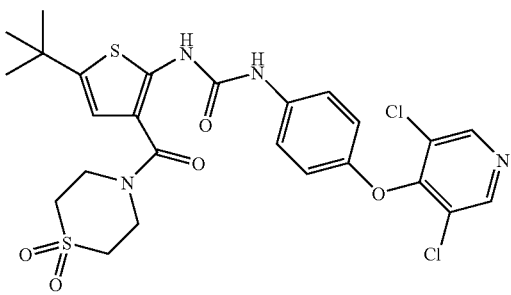

4-(3,5-Dichloropyridin-4-yloxy)benzenamine. To a vial containing 4-aminophenol (2.185 g, 20.0 mmol, 1 equiv.) in 60 mL DMF was added t-BuOK (2.468 g, 22.0 mmol, 1.1 equiv.) followed by 3,4,5-trichloropyridine (3.653 g, 20.0 mmol, 1 equiv.). The flask was fitted with a condenser and the mixture was stirred at 80° C. under nitrogen. After the reaction mixture was cooled, diluted with ethyl acetate (600 mL) and washed with water (3×150 mL) and brine. The organic layer was dried over Na2SO4, filtered and solvent was removed under vacuum. The crude material was absorbed onto silica gel and purified by flash column (7.5×12 cm silica) using 2500 mL 1:1 hexanes:ethyl acetate giving 4.6348 g (91%) of product as a light yellow crystalline solid.

5-tert-Butyl-2-(3-(4-(3,5-dichloropyridin-4-yloxy)phenyl)ureido)thiophene-3-carboxylic acid.

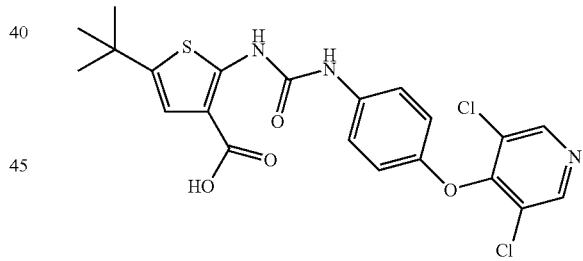

A vial containing 6-tert-butyl-1H-thieno[2,3-d][1,3]oxazine-2,4-dione and 4-(3,5-Dichloropyridin-4-yloxy)benzenamine in THF was capped and stirred at 80° C. After about 6 h, the reaction was cooled and enough solvent was removed under vacuum to leave an oil residue. Dichloromethane was added (ca. 10 mL) to precipitate product and the mixture was allowed to sit at least 1 h. The mixture was filtered (filter paper; vacuum suction) and the solids washed with dichloromethane. The solids on the filter and remaining in the flask were collected by dissolving in acetone. Solvent was removed under vacuum to give 89% of the product as a white fine crystalline solid.

The reaction was performed as above (method 1) to give 91% of the desired product as a light yellow oil. ¹H NMR (400 MHz, CD₃OD/CDCl₃): δ 8.50 (s, 2H), 7.39 (d, J=9.2 Hz, 2H), 6.76 (d, J=9.0 Hz, 2H), 6.47 (s, 1H), 4.08 (t, J=4.9 Hz, 4H), 3.12 (t, J=5.1 Hz, 4H), 1.31 (s, 9H).

Example 23

1-(5-tert-Butyl-3-(morpholine-4-carbonyl)thiophen-2-yl)-3-(4-(2-(methylcarbamoyl)pyridin-4-yloxy)phenyl)urea

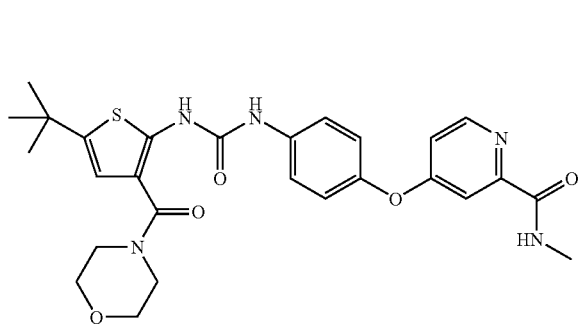

The compound of this example was prepared using a procedure analogous to that used in Example 11, except that 4-(4-aminophenoxy)-N-methylpicolinamide was used instead of 4-(pyridin-4-yloxy)aniline. $^1$H NMR: (400 MHz, CD$_3$OD) δ 8.40 (d, J=5.6 Hz, 1H), 7.54 (d, J=8.8 Hz, 2H), 7.52 (s, 1H), 7.04 (d, J=8.8 Hz, 2H), 6.97 (m, 1H), 6.58 (s, 1H), 3.66 (s, 8H), 2.91 (s, 3H), 1.33 (s, 9H).

Example 24

1-(5-tert-Butyl-3-(thiomorpholine-1,1-dioxide-4-carbonyl)thiophen-2-yl)-3-(4-(pyridin-4-ylmethyl)phenyl)urea

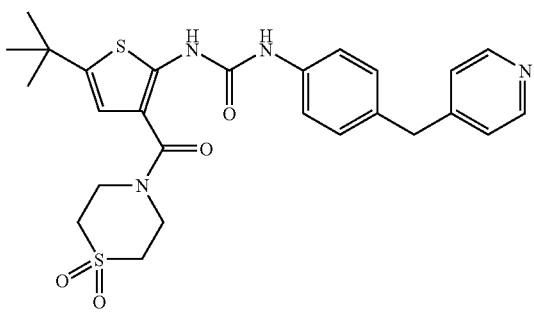

The compound of this example was prepared using a procedure analogous to that used in Example 5, except that 4-(pyridin-4-ylmethyl)aniline was used instead of 4-(4-aminophenoxy)-N-methylpicolinamide. $^1$H NMR: (400 MHz, DMSO-d$_6$) δ 9.63 (s, 1H), 9.49 (s, 1H), 8.36 (d, J=5.6 Hz, 2H), 7.30 (d, J=8.4 Hz, 2H), 7.14 (d, J=5.6 Hz, 2H), 7.08 (d, J=8.4 Hz, 2H), 6.58 (s, 1H), 3.84 (m, 4H), 3.81 (s, 2H), 3.19 (m, 4H), 1.23 (s, 9H).

Example 25

1-(2-tert-Butyl-4-(thiomorpholine-1,1-dioxide-4-carbonyl)thiazol-5-yl)-3-(4-(2-(methylcarbamoyl)pyridin-4-yloxy)phenyl)urea The compound of this example was prepared using a procedure analogous to that used in Example 18, except that 4-(4-aminophenoxy)-N-methyl-picolinamide was used instead of 4-(pyridin-4-yloxy)aniline. $^1$H NMR: (400 MHz, CD$_3$OD) δ 8.44 (d, J=5.6 Hz, 1H), 7.59 (d, J=8.8 Hz, 2H), 7.53 (d, J=2.4 Hz, 1H), 7.10 (d, J=8.8 Hz, 2H), 7.03 (dd, J=4.0, 1.2 Hz, 1H), 4.73 (m, 2H), 4.20 (m, 2H), 3.25 (m, 4H), 2.91 (s, 3H), 1.40 (s, 9H).

Example 26

Biological Activity of the Compounds

Human non-activated p38 kinase (MW=43 kDa) was purified according to the protocol described herein. Chemicals were purchased from Calbiochem. Fluorescence characterizations were conducted using a Cary Eclipse (Varian Analytical Instruments, Walnut Creek, Calif.). Research-grade CM5 sensor chips and coupling reagents (N-ethyl-N'-dimethylaminopropylcarbodiimide (EDC) N-hydroxysuccinimide (NHS), and 1 M ethanolamine HCl, pH 8.5) were purchased from Biacore AB (Uppsala, Sweden). The biosensor analyses were conducted using a Biacore 3000 SPR instrument. The kinetic analyses were carried on a Molecular Devices spectrophotometer (Molecular Devices Corporation, CA, USA).

P38 Kinase Assay. The protein kinase activity of p38 was determined by measuring the incorporation of $^{33}$P from γ-[$^{33}$P]ATP into the GST-ATF-2 substrate, amino acids 19-96 (Upstate, N.Y. USA). The reactions were carried out in a final volume of 50 μL of 24 mM Tris-HCl buffer, pH 7.5, containing 13 mM MgCl$_2$, 12% Glycerol, 2% DMSO, 2 mM DTT, 2.5 Ci of γ-[$^{33}$P]ATP (1000 Ci/mmol; 1 Ci=37 GBq) (AmershamBiosciense), 10 M ATP (AmershamBiosciense), and 2 M GST-ATF2. Compounds were preincubated with 10 nM p38 for 20 min at 30° C.; the reactions were initiated by the addition of GST-ATF2 and ATP and incubated for 70 min at 30° C. before being stopped by the addition of 10 μL of 600 mM phosphoric acid. The phosphorylated substrate was captured on phosphocellulose 96-well plate (Millipore MAPH-NOB 10), washed with 100 mM phosphoric acid, and counted in a BeckmenCoulter LS6500 liquid scintillation counter.

Abl Kinase activity: In a final reaction volume of 25 μL, Able (m) (5-10 mU) is incubated with mM MOPS pH 7.0, 0.2 mM EDTA, 50 μM EAIYAAPFAKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

CHK2 Kinase Activity: In a final reaction volume of 25 ml, CHK2 (h) (5-10 mU) is incubated with 8 mM MOPS pH 7.0, 0.2 mM EDTA, 200 mM KKKVASRSGLYRSPSMPENLN-RPR, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

c-RAF Kinase Activity: In a final reaction volume of 25 µl, c-RAF (h) (5-10 mU) is incubated with 25 mM Tris pH 7.5, 0.02 mM EGTA, 0.66 mg/ml myelin basic protein, 10 mM MgAcetate, and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

cSRC Kinase Activity: In a final reaction volume of 25 µl, cSRC (h) (5-'0 mU) is incubated with 8 mM MOPS pH 7.0, 0.2 mM EDTA, 250 µM KVEKIGEGTYGVVYK (Cdc2 peptide), 10 mM MgAcetate and [γ-$^{33}$P-ATP] (specific activity approx. 500 cpm/pmol, concentratin as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

EphB4 Kinase Activity: In a final reaction volume of 25 µl, EphB4 (h) (5-10 mU) is incubated with 8 mM MOPS pH 7.0, 0.2 mM EDTA, 10 mM MnCl$_2$, 0.1 mg/ml poly(Glue, Tyr) 4:1, 10 mM MgAcetate and [γ-$^{33}$P-ATP] (specific activity approx. 500 cpm/pmol, concentration as required). The reaction is initiated by the addition of the MgATP mix. After incubatin for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillating counting.

Flt3 Kinase Activity: In a final reaction volume of 25 µl, Flt3 (h) (5-10 mU) is incubated with 8 mM MOPS pH 7.0, 0.2 mM EDTA, 50 µM EAIYAAPFAKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 ml of a 3% phosphoric acid solution. 10 ml of the reaction is then spotted onto a P30 filtermat and washed three times for 5 minutes in 75 mM phosphoric acid and once in methanol prior to drying and scintillation counting.

GSK3β Kinase Activity: In a final reaction volume of 25 µl, GSK3β (h) (5-10 mU) is incubated with 8 µM MOPS pH 7.0, 0.2 mM EDTA, 20 mM YRRAAVPPSPSLSRHSSPHQS(p)EDEEE (phosphor GS2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 50 mM phosphoric acid and once in methanol prior to drying and scintillation counting.

IGF-1R Kinase Activity In a final reaction volume of 25 µl, IGF-1R (h) (5-10 mU) is incubated with 50 mM Tris pH 7.5, 0.1 mM EGTA, 0.1 mM Na$_3$VO$_4$, 0.1% β-mercaptoethanol, 250 µM KKKSPEGYVNIEFG, 10 mM MnCl$_2$, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

JNK2α2 Kinase Activity: In a final reaction volume of 25 µl, JNK2α2 (h) (5-10 mU) is incubated with 50 mM Tris pH 7.5, 0.1 mM EGTA, 0.1% β-mercaptoethanol, 3 µM ATF2, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

JNK3 Kinase Activity: In a final reaction volume of 25 µl, JNK3 (h) (5-10 mU) is incubated with 50 mM Tris pH 7.5, 0.1 mM EGTA, 0.1% β-mercaptoethanol, 250 µM peptide, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Lck Kinase Activity: In a final reaction volume of 25 ml, Lck (h) (5-10 mU) is incubated with 50 mM Tris pH 7.5, 0.1 mM EGTA, 0.1 mM Na$_3$VO$_4$, 250 µM KVEKIGEGTYGV-VYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Lyn Kinase Activity: In a final reaction volume of 25 µl, Lyn (h) (5-10 mU) is incubated with 50 mM Tris pH 7.5, 0.1 mM EGTA, 0.1 mM Na$_3$VO$_4$, 0.1% β-mercaptoethanol, 0.1 mg/ml poly(Glue, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

MAPKAP-K2 Kinase Activity: In a final reaction volume of 25 μl, MAPKAP-K2 (h) (5-10 mU) is incubated with 50 mM Na-β-glycerophosphate pH 7.5, 0.1 mM EGTA, 30 mM KKLNRTLSVA, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Met Kinase Activity: In a final reaction volume of 25 μl, Met (h) (5-10 mU) is incubated with 8 mM MOPS pH 7.0, 0.2 mM EDTA, 250 μM KKKSPEGYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

PDGFRβ Kinase Activity: In a final reaction volume of 25 μl, PDGFRβ (h) (5-10 mU) is incubated with 8 mM MOPS pH 7.0 0.2 mM EDTA, 0.1 mg/ml poly(Glu, Tyr) 4:1, 10 mM MnCl$_2$, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

PKA Kinase Activity: In a final reaction volume of 25 μl, PKA (b) (5-10 mU) is incubated with 8 mM MOPS pH 7.0, 0.2 mM EDTA, 30 μM LRRASLG (Kemptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is the spotted onto a P30 filtermat and washed three times for 5 minutes in 50 mM phosphoric acid and once in methanol prior to drying and scintillation counting.

PKCα Kinase Activity: In a final reaction volume of 25 μl, PKCα (h) (5-10 mU) is incubated with 20 mM HEPES pH 7.4, 0.03% Triton X-100, 0.1 mM CaCl$_2$, 0.1 mg/ml phosphatidylserine, 10 μg/ml diacylglycerol, 0.1 mg/ml histone Hi, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

SAPK2a Kinase Activity: In a final reaction volume of 25 μl, SAPK2a (h) (5-10 mU) is incubated with 25 mM Tris pH 7.5, 0.02 mM EGTA, 0.33 mg/ml myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is the spotted onto a P30 filtermat and washed three times for 5 minutes in 75 mM phosphoric acid and once in methanol prior to drying and scintillation counting.

SAPK2b Kinase Activity: In a final reaction volume of 25 μl, SAPK2b (h) (5-10 mU) is incubated with 25 mM Tris pH 7.5, 0.02 mM EGTA, 0.33 mg/ml myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is the spotted onto a P30 filtermat and washed three times for 5 minutes in 75 mM phosphoric acid and once in methanol prior to drying and scintillation counting.

SAPK3 Kinase Activity: In a final reaction volume of 25 μl, SAPK3 (h) (5-10 mU) is incubated with 25 mM Tris pH 7.5, 0.02 mM EGTA, 0.33 mg/ml myelin basic protein, 10 mM MgAcetate and [γ-$^{33}$P-ATP] (specific activity approx. 500 cpm/®mol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is the spotted onto a P30 filtermat and washed three times for 5 minutes in 75 mM phosphoric acid and once in methanol prior to drying and scintillation counting.

SAPK4 Kinase Activity: In a final reaction volume of 25 μl, SAPK4 (h) (5-10 mU) is incubated with 25 mM Tris pH 7.5, 0.02 mM EGTA, 0.33 mg/ml myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μL of the reaction is the spotted onto a P30 filtermat and washed three times for 5 minutes in 75 mM phosphoric acid and once in methanol prior to drying and scintillation counting.

Tie2 Kinase Activity: In a final reaction volume of 25 μl, Tie2 (h) (5-10 mU) is incubated with 8 mM MOPS pH 7.0, 0.2 mM EDTA, 0.5 mM MnCl$_2$, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

TrkB Kinase Activity: In a final reaction volume of 25 μl, TrkB (h) (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

The protein kinase inhibitory results for Compound 3 are shown in the following table.

| Protein | % Inhibition at 2 μm |
|---|---|
| c-RAF | 76-100 |
| Flt3 | 76-100 |
| JNK2a2 | 26-50 |
| JNK3 | 0-25 |
| LCK | 51-75 |
| Lyn | 76-100 |
| p38α | 76-100 |
| p38β | 76-100 |
| p38γ | 76-100 |
| p38δ | 76-100 |
| Tie2 | 76-100 |
| TrkB | 76-100 |

The kinase inhibition activity for the compounds of Examples 1, 2, and 4 are shown in the following table.

| | Kinase Activity Results - % Inhibition at ATP $K_{m,app}$ | | |
|---|---|---|---|
| | Compound (2 μM) | | |
| Kinase | Example 1 | Example 2 | Example 4 |
| Abl1 | 0-25 | 0-25 | 0-25 |
| Akt1 | 0-25 | 0-25 | 0-25 |
| CK2-alpha 1 | 0-25 | 0-25 | 0-25 |
| c-MET | 0-25 | 26-50 | 0-25 |
| EGFR | 0-25 | 0-25 | 0-25 |
| EphB4 | 76-100 | 76-100 | 76-100 |
| ERK2 | 0-25 | 0-25 | 0-25 |
| FGFR1 | 0-25 | 0-25 | 26-50 |
| Flt3 | 76-100 | 76-100 | 76-100 |
| GSK3-beta | 0-25 | 0-25 | 0-25 |
| IGF1R | 0-25 | 0-25 | 0-25 |
| IRAK4 | 0-25 | 0-25 | 0-25 |
| Lck | 0-25 | 0-25 | 0-25 |
| LynA | 26-50 | 26-50 | 51-76 |
| MAPKAP-K2 | 0-25 | 0-25 | 0-25 |
| PDGFR-beta | 26-50 | 26-50 | 26-50 |
| PKA | 0-25 | 0-25 | 0-25 |
| PKC-alpha | 0-25 | 0-25 | 0-25 |
| Src | 0-25 | 0-25 | 0-25 |

The compounds of Examples 1 and 2 were also tested for cell growth inhibition activity a gains two cell lines, MCF-7 and U266. Jurkat cells, suspended in RPMI 1640 media, supplemented with 10% FBS, were pipetted into 96-well plates at a density of 10,000 cells per milliliter in a volume of 200 mL per well. Cells were allowed to equilibrate overnight at 37 C in 5% $CO_2$. Cells were then incubated in the presence of the test compound at a concentrations ranging from 0.03 μM to 10 μM (at ½ log dilutions) for 24 hours. After the incubation period, cells were assessed for viability using either WST-1 (Biovision) or Alamar Blue (BioSourse). Values from treated cells were compared to values from control cells and values expressed as percent control. The compounds of Examples 1 and 2 and $IC_{50}$ values of lower than 10 μM.

The protein kinase inhibitory results for the compound of Example 3 are shown in the following table.

| Kinase | Species | Rate (μM) | % Control |
|---|---|---|---|
| cRaf | Human | 2 | 76-100 |
| DDR2 | Human | 2 | 76-100 |
| EphA1 | Human | 2 | 76-100 |
| EphA2 | Human | 2 | 76-100 |
| EphA3 | Human | 2 | 76-100 |
| EphA5 | Human | 2 | 76-100 |
| EphA7 | Human | 2 | 76-100 |
| EphA8 | Human | 2 | 76-100 |
| FGFR1 | Human | 2 | 76-100 |
| FGFR2 | Human | 2 | 51-75 |
| Flt3 | Human | 2 | 76-100 |
| Flt1 | Human | 2 | 76-100 |
| Hck | Human | 2 | 76-100 |
| JNK2α2 | Human | 2 | 26-50 |
| KDR | Human | 2 | 76-100 |
| Lck | Human | 2 | 51-75 |
| Lyn | Human | 2 | 76-100 |
| Lyn | Mouse | 2 | 76-100 |
| MINK | Human | 2 | 51-75 |
| MKK6 | Human | 2 | 76-100 |
| Mnk2 | Human | 2 | 76-100 |
| MuSK | Human | 2 | 76-100 |
| P38b | Human | 2 | 76-100 |
| P38a | Human | 2 | 76-100 |
| P38g | Human | 2 | 76-100 |
| P38d | Human | 2 | 76-100 |
| P70S6K | Human | 2 | 51-75 |
| Pyk2 | Human | 2 | 51-75 |
| Ret | Human | 2 | 76-100 |
| ROCKI | Human | 2 | 51-75 |
| ROCKI | Rat | 2 | 51-75 |
| Ros | Human | 2 | 76-100 |
| TAK1 | Human | 2 | 76-100 |
| Tie2 | Human | 2 | 76-100 |
| TrkA | Human | 2 | 76-100 |
| TrkB | Human | 2 | 76-100 |

Additionally, a number of the compounds were tested for activity for inhibiting Flt3, KDR, Tie2, and p38. The compounds exhibiting acceptable biological activity, for example $IC_{50}$'s of less than 1 μM for Flt3, of >10 to less than 0.1 μM for KDR, of >10 to less than 1 μM for Tie2, and less than 1 μM for p38.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound selected from the group consisting of
   1-[5-tert-butyl-3-(1,1-dioxo-1λ⁶-[1,2,5]thiadiazepane-5-carbonyl)thiophen-2-yl]-3-[4-(pyridin-4-yloxy)phenyl]urea;
   1-[5-tert-butyl-3-(3-oxo-piperazine-1-carbonyl)thiophen-2-yl]-3-[4-(pyridin-4-yloxy)phenyl]urea;
   1-[5-tert-butyl-3-(1,1-dioxo-1λ⁶-thiomorpholine-4-carbonyl)thiophen-2-yl]-3-[4-(pyridin-4-yloxy)phenyl]urea; and
   1-[5-tert-butyl-3-(5-oxo-[1,4]diazepane-1-carbonyl)thiophen-2-yl]-3-[4-(pyridin-4-yloxy)phenyl]urea;
   or pharmaceutically acceptable salt thereof.

* * * * *

UNITED STATES PATENT AND TRADEMARK OFFICE
CERTIFICATE OF CORRECTION

PATENT NO.        : 7,612,200 B2                                    Page 1 of 1
APPLICATION NO. : 11/295433
DATED             : November 3, 2009
INVENTOR(S)       : Michelotti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this

Nineteenth Day of October, 2010

David J. Kappos
*Director of the United States Patent and Trademark Office*